United States Patent [19]

Christensen et al.

[11] 4,235,917
[45] Nov. 25, 1980

[54] N-ALKYL-N-ACYL DERIVATIVES OF THIENAMYCIN

[75] Inventors: Burton G. Christensen, Metuchen; William J. Leanza, Berkeley Heights, both of N.J.

[73] Assignee: Merck & Co., Inc., Rahway, N.J.

[21] Appl. No.: 793,974

[22] Filed: May 5, 1977

[51] Int. Cl.³ .................... A61K 31/40; C07D 487/04
[52] U.S. Cl. ........................... 424/274; 260/245.2 T; 424/250; 424/263; 424/269; 424/270; 424/272; 424/273 R; 542/420; 542/426; 542/427; 546/272; 546/122
[58] Field of Search .................... 260/326.31, 245.2 T; 424/274

[56] References Cited

U.S. PATENT DOCUMENTS 3,950,357  4/1976  Kahan et al. .................... 260/326.31
4,150,145  4/1979  Christinsen et al. ............ 260/326.31

OTHER PUBLICATIONS

Beecham Group Ltd., Derwent Abstract 72175x 3/16/75.
Beecham Group Ltd., Derwent Abstract 67721w 3/28/74.
Merck & Co. Inc., Derwent Abstract 40282y 11-19-76.
Merck & Co. Inc., Derwent Abstract 40283y 11-19-76.

*Primary Examiner*—Mary C. Lee
*Attorney, Agent, or Firm*—Frank M. Mahon; Julian S. Levitt; James A. Arno

[57] ABSTRACT

Disclosed are N-alkyl- N-acyl derivatives of the antibiotic thienamycin having the following structural formula:

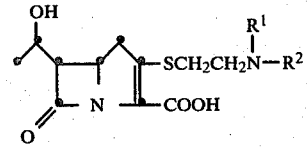

wherein $R^1$ is, inter alia, alkyl, alkenyl, aryl or aralkyl; and $R^2$ is acyl. Such compounds, including their O- and carboxyl derivatives are useful as antibiotics. Also disclosed are processes for the preparation of such compounds, pharmaceutical compositions comprising such compounds, and methods of treatment comprising administering such compounds and compositions when an antibiotic effect is indicated.

6 Claims, No Drawings

N-ALKYL-N-ACYL DERIVATIVES OF THIENAMYCIN

BACKGROUND OF THE INVENTION

This invention relates to novel N-alkyl-N-acyl derivatives (I) of the antibiotic thienamycin (structure II, below). Such compounds, including their O- and carboxyl derivatives and their pharmaceutically acceptable salts are useful as antibiotics. This invention also relates to processes for the preparation of such compounds, pharmaceutical compositions comprising such compounds, and methods of treatment comprising administering such compounds and compositions when an antibiotic effect is indicated. The compounds of the present invention may generically be represented by the following structural formula (I):

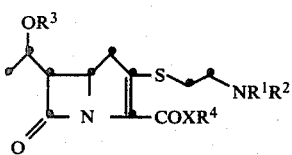

or, more conveniently, by the symbol:

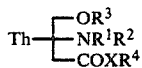

wherein:
"Th" symbolizes the bicyclic nucleus of thienamycin and the OH, amino, and carboxyl groups of thienamycin are illustrated;

$R^2$ is acyl (the term "acyl" is by definition inclusive of the alkanoyls including derivatives and analogues thereof such as thio analogues wherein the carbonyl oxygen is replaced by sulphur, as well as the sulphur and phosphorous acyl analogues such as substituted sulfonyl-, sulfinyl- and sulfenyl- radicals and substituted P (III and V) radicals such as the substituted phosphorous-, phosphoric-, phosphonous- and phosphonic- radicals, respectively; such acyl radicals of the present invention are further defined below);

X is oxygen, sulphur or NR' (R'=H or alkyl having 1–6 carbon atoms); and $R^4$ is, inter alia, representatively selected from the group consisting of hydrogen, conventional blocking groups such as trialkylsilyl, acyl and radicals ($R^4$) giving rise to the pharmaceutically acceptable salt, ester and amide moieties (—$COXR^4$) known in the bicyclic β-lactam antibiotic art (the definition of $R^4$ is given in greater detail below);

$R^3$ is hydrogen; or $R^3$ is (1) acyl (generically the group $OR^3$ is classifiable as an ester); or (2) $R^3$ is selected from alkyl, aryl, aralkyl and the like (such that the group $OR^3$ is generically classifiable as an ether); the term "acyl" is by definition inclusive of the alkanoyls including derivatives and analogues thereof such as thio analogues wherein the carbonyl oxygen is replaced by sulphur; as well as sulphur and phosphorous acyl analogues such as substituted sulfonyl-, sulfinyl-, and sulfenyl- radicals, and substituted P (III and V) radicals such as substituted phosphorous-, phosphoric-, phosphonous- and phosphonic- radicals, respectively; such acyl radicals of the present invention are further defined below, as are the radicals (2, above) which constitute the ether embodiments of the present inventon; and $R^1$ is, inter alia, alkyl, alkenyl, aryl or aralkyl; for example, $R^1$ may be selected from the group consisting of: substituted and unsubstituted: lower alkyl having 1–10 carbon atoms, alkenyl having 2–10 carbon atoms, alkynyl having 2–10 carbon atoms, ring substituted and unsubstituted: cycloalkyl, cycloalkenyl, cycloalkenylalkyl, and cycloalkylalkyl having 3–6 ring carbon atoms and 1–6 carbon atoms in the alkyl chain; aryl having 6–10 carbon atoms; aralkyl having 6–10 ring carbon atoms, and 1–6 carbon atoms in the alkyl chain; mono- and bicyclic heteroaryl and heteroaralkyl comprising 4–10 ring atoms one or more of which is selected from oxygen, nitrogen and sulphur and 1–6 carbon atoms in the alkyl chain; and wherein the ring or chain substituent (or substituents) in the aforementioned radicals is selected from: halo such as chloro, bromo, iodo and fluoro, azido, cyano, amino, mono-, di- and trialkyl substituted amino wherein the alkyl has 1–6 carbon atoms, hydroxyl, alkoxyl having 1–6 carbon atoms, alkylthioalkyl having 1–6 carbon atoms, carboxyl, oxo, alkoxycarbonyl having 1–6 carbon atoms in the alkoxyl moiety, acyloxy comprising 2–10 carbon atoms, carbamoyl, and mono- and dialkylcarbamoyl wherein the alkyl groups have 1–4 carbon atoms, cyanothio (—SCN), and nitro;

$R^1$ is further defined below.

Thienamycin, a convenient starting material for the preparation of the compounds of the present invention, is disclosed and claimed in U.S. Pat. No. 3,950,357, issued Apr. 13, 1976. This patent is incorporated herein by reference for the disclosure relative to the preparation and isolation of thienamycin. Thienamycin is known to have the following structure (II):

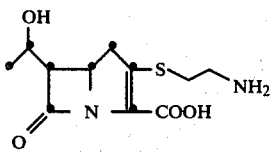

Starting material II (including all isomers and mixtures of isomers thereof) is also available by the total synthesis which is described and claimed in co-pending, commonly assigned U.S. patent application Ser. No. 792,071, filed Apr. 28, 1977, of Christensen, Johnston and Schmitt, now abandoned. This application is incorporated herein by reference since it makes available all isomers, pure and as mixtures, of II which are suitable starting materials for the preparation of the compounds of the present invention. Another convenient starting material for preparation of the compounds of the present invention is N-alkylated thienamycin and its O- and carboxyl derivatives (III):

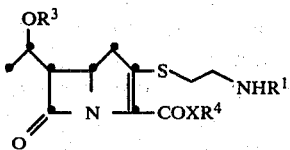

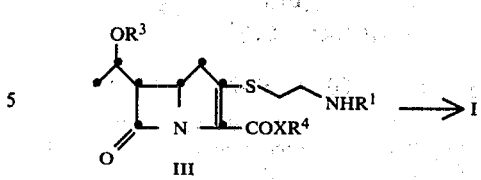

wherein $R^3$, X, $R^4$ and $R^1$ are as defined above. The N-alkylated thienamycins (III) are disclosed and claimed in co-pending, commonly assigned U.S. patent application Ser. No. 733,611 filed Oct. 18, 1976, now abandoned. This application is incorporated herein by reference for its disclosure relative to the preparation of N-alkyl thienamycins defined by III, above.

There is a continuing need for new antibiotics. For unfortunately there is no static effectiveness of a given antibiotic because continued wide scale usage of any such antibiotic selectively gives rise to resistant strains of pathogens. In addition, the known antibiotics suffer from the disadvantage of being effective only against certain types of microorganisms. Accordingly the search for new antibiotics continues.

Unexpectedly, it has been found that the compounds of the present invention are broad spectrum antibiotics, which are useful in animal and human therapy and in inanimate systems.

Thus, it is an object of the present invention to provide a novel class of antibiotics which possess the basic nuclear structure of the antibiotic thienamycin but which are characterized as N-alkyl-N-acyl derivatives thereof. These antibiotics are active against a broad range of pathogens which representatively include gram positive bacteria such as *S. aureus, Strep. pyogenes* and *B. subtilis* and gram negative bacteria such as *E. coli, Proteus morganii,* Serratia and Klebsiella. Further objects of this invention are to provide chemical processes for the preparation of such antibiotics and their non-toxic pharmaceutically acceptable salts; pharmaceutical compositions comprising such antibiotics; and to provide methods of treatment comprising administering such antibiotics and composition when an antibiotic effect is indicated.

DETAILED DESCRIPTION OF THE INVENTION

With respect to the generic description of the present invention (structure I, above) and most preferred embodiments are those wherein $R^1$ is selected from lower alkyl and alkenyl having from 1 to 6 carbon atoms; such as methyl, ethyl, propyl, allyl and the like; benzyl and nuclear substituted benzyl such as p-t-butyl benzyl and the like; heteroaralkyls such as 4-pyridyl methyl, 2-furyl methyl, 2-thienyl methyl and the like; and $R^3$, $R^2$, X and $R^4$ are as defined above and further exemplified below. Especially preferred compounds of the present invention are those wherein $R^1$ and $R^2$ are as defined in this paragraph; X is oxygen, $R^3$ is hydrogen, and $R^4$ is hydrogen or a pharmaceutically acceptable salt.

The compounds of the present invention are most conveniently prepared by the N-acylation of an N-alkylated thienamycin:

Appropriate N-acylation procedures (III→I) are fully disclosed in co-pending, commonly assigned U.S. patent application Ser. No. 733,653 filed Oct. 18, 1976 which application discloses and claims N-acyl thienamycin (IV) and methods for their preparation from thienamycin (II):

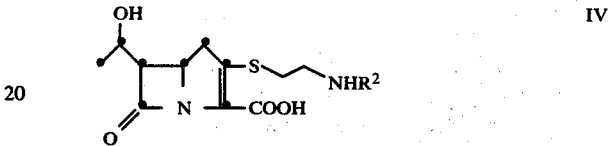

wherein $R^2$ is acyl. Since the N-acylation procedures of the cited application are strictly analogous to the above-defined acylation (III→I), this co-pending application is incorporated herein by reference for its disclosure relative thereto.

The starting material III is fully disclosed and claimed in co-pending, commonly assigned U.S. patent application Ser. No. 733,611 filed Oct. 18, 1976, now abandoned. This co-pending application is thus incorporated herein by reference for its disclosure relative to the preparation of N-monoalkyl thienamycin derivatives (III).

Such N-monoalkyl thienamycin derivatives are prepared by reacting thienamycin or a suitable derivative thereof or a suitably protected thienamycin species with an N-alkylating agent. There is no undue criticality in the process of any of a variety of well-known N-alkylation procedures may be employed. The identity of the N-alkylating agent is a matter of choice within the limits set by the definition of $R^1$. The N-alkylation may be conducted in any of a variety of solvent systems which are inert or substantially inert to the desired course of reaction. Suitable solvents include polar solvents such as water, lower alkanols such as ethanol, dioxane, tetrahydrofuran (THF), acetonitrile, hexamethylphosphoramide (HMPA), dimethylformamide (DMF) and the like and mixtures (particularly aqueous mixtures) of the above; and non-polar solvents such as benzene and halohydrocarbons such as methylene chloride, chloroform and the like. Typically the reaction is conducted at a temperature of from −40° C. to 50° C. for from 15 minutes to 5 hours. Usually, the reaction is conducted in the presence of an acid acceptor such as propylene oxide, magnesium oxide, potassium carbonate and the like. The preferred N-alkylating agents include active halides, sulfate esters, and Michael addition reagents. The following reagents are representative of such alkylating agents: methyl iodide, allyl bromide, bromo acetone, phenacyl bromide, benzyl bromide, ethylchloroacetate, propargyl bromide, 2-bromoethylethylether, dimethyl sulfate, ethyl fluorosulphonate, methylfluorosulphonate, chloromethylthiocyanate, chloroethylmethylsulfide, bromoethylcyclopropane, 2,4-dinitrofluorobenzene, 2-chloromethylpyridine, acrylonitrile, methyl methacrylate, nitroethylene and the like.

The starting material III, may be prepared in any of a variety of ways. One convenient starting material is tris-trimethylsilyl thienamycin [Th(TMS)₃] (see below). When it is desired for R³, R⁴ or R³ and R⁴ to be other than hydrogen, suitably derivatized starting materials such as Ia, Ib and Ic (below), may be employed.

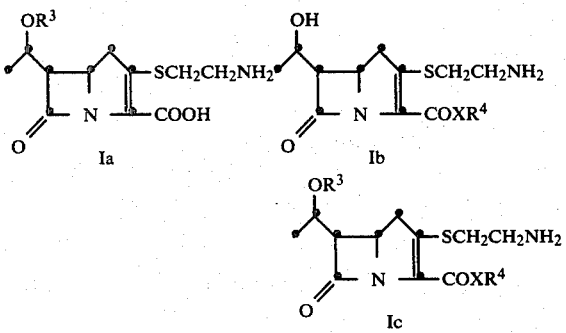

wherein R³, X and R⁴ are as defined above and further exemplified below. Starting materials Ia, Ib and Ic, which are also useful as antibiotics, are disclosure and claimed in co-pending, concurrently filed U.S. patent application Ser. Nos. 733,655, 733,651, 733,652, respectively; all filed Oct. 18, 1976, all now abandoned. These applications are incorporated herein by reference since they describe useful starting materials for preparing III, and, additionally, analogous processes for converting the N-alkylated N-acylated thienamycins of the present invention to carboxyl-, O-; and carboxyl- and O-derivatized forms which are also embraced by the present invention and are useful as antibiotics.

As stated above the N-alkylation is carried out in any of the above-named solvents in the presence of the N-alkylating agent of choice, such as R¹X′, wherein X′ is a leaving group such as halo or a sulfate ester. When using, for example, the above mentioned Th(TMS)₃ then the desired product is obtained by aqueous hydrolysis following the N-alkylation step. The following reaction diagram summarizes the process:

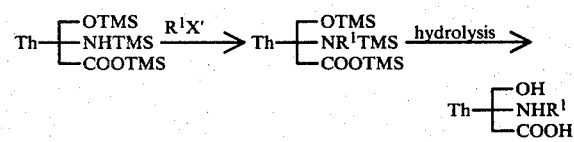

wherein TMS is trimethylsilyl, and R¹ and X′ are as defined above.

A second scheme for the preparation of monoalkyl thienamycins (III) involves the N-alkylation of an N-substituted thienamycin wherein the substituent is an easily removable, bulky group (R°) such as an aralkyl group, for example substituted and unsubstituted: benzyl, benzylhydryl (—CH(C₆H₅)₂) and trityl (—C(C₆H₅)₃) wherein the ring substituent on the aralkyl may be halo, nitro, loweralkyl, loweralkoxyl or the like. The following reaction diagram summarizes this scheme:

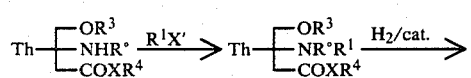

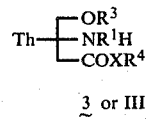

wherein all symbolism is as defined above.

In words relative to the above diagram, starting material 1, prepared for example from the reaction of thienamycin or derivative thereof with an aralkyl halide, is reacted with the N-alkylating agent of choice R¹X′, as above-described, to provide the N,N-dialkyl intermediate 2. The aralkyl N-substituent R° is readily removable to produce 3 by hydrogenolysis. Suitable conditions for this final cleavage step involve hydrogenating 2 in a solvent such as ethanol under hydrogen (1 to 4 atmospheres) in the presence of a catalyst such as platinum, palladium, or oxides thereof. The ultimate product of this reaction is primarily 3, the N-monoloweralkyl species. However, there is some co-presence of N,N-diloweralkyl theinamycin. Such contaminating by-products may be separated by chromatographic methods and the magnitude of contamination may be minimized by employing one equivalent or less of the alkylating agent R¹X′.

A third method for the preparation of N-monoalkyl species, III, particularly N-loweralkyl species, is similar to the above described procedure except that the starting material 1a is N,N-diaralkyl thienamycin. The preparation of such starting materials is described in incorporated by reference U.S. patent application Ser. No. 733,611, filed Oct. 18, 1976, now abandoned. The following reaction diagram summarized this process:

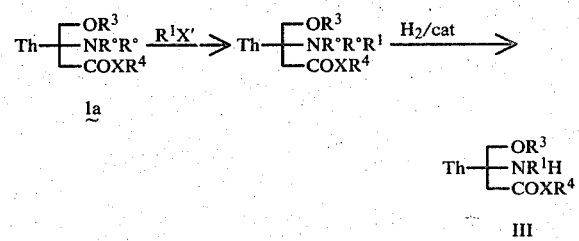

wherein all symbolism is as described above. It is to be noted that this scheme for the preparation of N-loweralkyl thienamycins is not complicated by the co-preparation of N,N-diloweralkyl thienamycins.

A fourth method which is particularly suitable for the preparation of N-loweralkyl thienamycins species (III) involves the N-alkylation of a Schiff's Base of thienamycin. The following diagram summarizes the reaction.

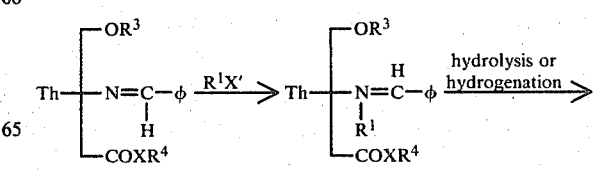

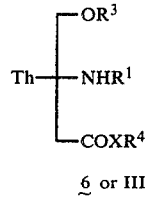

wherein all symbolism is as previously defined and in addition φ is phenyl, $R^4$ and $R^3$ may be the trimethylsilyl radical (TMS) and X may be oxygen. The preferred Schiff's base is that obtained by reacting thienamycin with benzaldehyde or nuclear substituted benzaldehyde. There is no criticality in the process for preparing such Schiff's bases and their preparation is disclosed in co-pending, commonly assigned U.S. patent application Ser. No. 733,656 filed Oct. 18, 1976, now abandoned. This co-pending application is incorporated herein by reference as it describes the preparation of starting material 4. The reaction of 4 with the alkylating reagent $R^1X'$ provides intermediate 5 which upon aqueous hydrolysis or catalytic hydrogenolysis provides the desired N-loweralkyl thienamycin species 6.

A fifth method for preparing N-loweralkyl thienamycins (III) involves the desulfurization of an N-thioacyl thienamycin in the presence of a hydrogenation catalyst such as Raney Nickel:

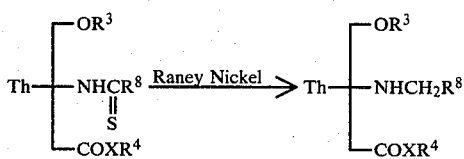

wherein X is oxygen, $R^3$ and $R^4$ are as previously defined but preferably are hydrogen, and $R^8$ is hydrogen, aryl or a lower alkyl moiety having 1–5 carbon atoms. The N-thioacyl thienamycin starting materials are fully disclosed in co-pending U.S. patent application Ser. No. 733,653 filed Oct. 18, 1976, now abandoned, which application is incorporated herein by reference for its disclosure relative to the preparation of such starting materials. The above desulfurization is typically conducted in polar protic solvents such as water, lower alkanols such as ethanol, and aqueous mixtures thereof at a temperature of from 0°–50° C. for from 2 minutes to 5 hours.

Identification of the Radical —COXR⁴

In the generic representation of the compounds of the present invention (I, above), the radical represented by —COXR⁴, is, inter alia, —COOH (X is oxygen and $R^4$ is hydrogen) and all radicals known to be effective as pharmaceutically acceptable salt, ester, anhydride ($R^4$ is acyl) and amide radicals in the bicyclic β-lactam antibiotic art, such as the cephalosporins and penicillins and the nuclear analogues thereof.

Suitable radicals ($R^4$) include conventional protecting or carboxyl blocking groups. The term "blocking group" as utilized herein is employed in the same manner and in accordance with the teaching of U.S. Pat. No. 3,697,515 which is incorporated herein by reference. Pharmaceutically acceptable thienamycin derivatives of the present invention falling in this class are given below. Suitable blocking esters thus include those selected from the following list which is representative and not intended to be an exhaustive list of possible ester groups, wherein X=0 and $R^4$ is given:

(i) $R^4 = CR^aR^bR^c$ wherein at least one of $R^a$, $R^b$ and $R^c$ is an electron-donor, e.g., p-methoxyphenyl, 2,4,6-trimethylphenyl, 9-anthryl, methoxy, $CH_2SCH_3$, tetrahydrofury-2-yl, tetrahydropyran-2-yl or fur-2-yl. The remaining $R^a$, $R^b$ and $R^c$ groups may be hydrogen or organic substituting groups. Suitable ester groups of this type include p-methoxybenzyloxycarbonyl and 2,4,6-trimethylbenzyloxycarbonyl.

(ii) $R^4 = CR^aR^bR^c$ wherein at least one of $R^a$, $R^b$ and $R^c$ is an electron-attracting group, e.g., benzoyl, p-nitrophenyl, 4-pyridyl, trichloromethyl, tribromomethyl, iodomethyl, cyanomethyl, ethoxycarbonylmethyl, arylsulphonylmethyl, 2-dimethylsulphoniummethyl, o-nitrophenyl or cyano. Suitable esters of this type include benzoylmethoxycarbonyl, p-nitrobenzyloxycarbonyl, 4-pyridylmethoxycarbonyl, 2,2,2-trichloroethoxycarbonyl and 2,2,2-tribromoethoxycarbonyl.

(iii) $R^4 = CR^aR^bR^c$ wherein at least two of $R^a$, $R^b$ and $R^c$ are hydrocarbon such as alkyl, e.g., methyl or ethyl, or aryl, e.g., phenyl and the remaining $R^a$, $R^b$ and $R^c$ group, if there is one, is hydrogen. Suitable esters of this type include t-butyloxycarbonyl, t-amyloxycarbonyl, diphenylmethoxycarbonyl and triphenylmethoxycarbonyl.

(iv) $R^4 = R^d$, wherein $R^d$ is adamantyl, 2-benzyloxyphenyl, 4-methylthiophenyl or tetrahydropyran-2-yl.

Silyl esters, under this category or blocking groups, may conveniently be prepared from a halosilane or a silazane of the formula: $R^{4'}_3SiX'$; $R^{4'}_2SiX'_2$; $R^{4'}_3Si.NR^{4'}_2$; $R^{4'}_3Si.NH.COR^{4'}$; $R^{4'}_3Si.NH.CO.NH.SiR^{4'}_3$; $R^{4'}NH.CO.NH.SiR^{4'}_3$; or $R^{4'}C(OSiR^{4'}_3)$; $HN(SiR^{4'}_3)_2$ wherein X' is a halogen such as chloro or bromo and the various groups $R^{4'}$, which can be the same or different, represent hydrogen atoms or alkyl, e.g., methyl, ethyl, n-propyl, iso-propyl; aryl, e.g., phenyl; or aralkyl, e.g., benzyl groups.

More generally stated, pharmaceutically acceptable carboxyl derivatives of the present invention are those derived by reacting thienamycin or an N-protected thienamycin such as III or an N-acylated thienamycin, or a species of the present invention I with alcohols, phenols, mercaptans, thiophenols, acylating reagents and the like. Such starting materials or embodiments of the present invention may be derivatized to establish the $R^3$ group of of the compounds of the present invention (I, above). For example, esters and amides of interest are the compounds of the formula I (above) having the following group at the 2-position: —COXR⁴ wherein X is oxygen, sulfur, or NR' (R' is H, alkyl or aryl) and $R^4$ is alkyl having 1–10 carbon atoms, straight or branched, such as methyl, ethyl, t-butyl, pentyl, decyl and the like; carbonylmethyl, including phenacyl, p-bromo-phenacyl, t-t-butylphenacyl, acetoxyacetylmethyl, pivaloxyacetylmethyl, carboxymethyl, and its alkyl and aryl esters, α-carboxy-α-isopropyl; aminoalkyl including 2-methylaminoethyl, 2-diethylaminoethyl, 2-acetamidoethyl, phthalimidomethyl, succinimidomethyl, alkoxyalkyl wherein the alkoxy portion has 1–10 and preferably 1–6 carbon atoms; but can be branched, straight or cyclic, and the alkyl portion has 1–6 carbon atoms, such as methoxymethyl, ethoxymethyl, isopropoxymethyl, decyloxymethyl, ethoxypropyl, decyloxypentyl, cyclohexyloxymethyl and the like; alkanoyloxyalkyl wherein the alkanoyloxy portion is straight or branched and has 1–6 carbon atoms and the alkyl portion has 1–6 carbon atoms, such as acetoxymethyl, pivaloyloxymethyl, acetoxyethyl, propionyloxyethyl, acetoxypropyl, and the like; haloalkyl wherein halo is chloro, bromo, fluoro, or iodo, and the alkyl portion is straight or branched having 1–6 carbon atoms, e.g., 2,2,2-trichloroethyl, trifluoroethyl, 2-bromopropyl, diiodomethyl, 2-chloroethyl, 2-bromoethyl, and the like; alkenyl having 1–10 carbon atoms, either straight or branched, e.g., allyl, 2-propenyl, 3-butenyl, 4-butenyl, 4-pentenyl, 2-butenyl, 3-pentenyl, 3-methyl-3-butenyl, metallyl, 1,4-cyclohexadien-1-yl-methyl, and the like alkynyl having 1–10 carbon atoms, either straight or branched e.g., 3-pentenyl, propargyl, ethynyl, 3-butyn-1-yl, and the like; alkanoyl, either straight or branched, having 1–10 carbon atoms, such as pivaloyl, acetyl, propionyl, and the like; aralkyl or heteroaralkyl wherein alkyl has 1–3 carbon atoms, and hetero means 1–4 hetero atoms being selected from the group consisting of O, S, or N, such as benzyl, benzhydryl, and substituted benzyl, benzhydryl, or e.g., benzyl or benzhydryl substituted with 1–3 substituents such as benzyl, phenoxy, halo, loweralkyl, loweralkanoyloxy of 1–5 carbon atoms, lower alkoxy, hydroxy, nitro, blocked carboxy, or combinations thereof, e.g., p-chlorobenzyl, o-nitrobenzyl, 3,5-dinitrobenzyl, p-methoxybenzyl, m-benzoylbenzyl, p-t-butylbenzyl, m-phenoxybenzyl, p-benzoylbenzyl, p-nitrobenzyl, 3,5-dichloro-4-hydroxybenzyl, p-methoxycarbonylbenzyl, p-methoxybenzhydryl, p-carboxybenzyl, the latter being either the free acid, ester or the sodium salt, 2,4,6-trimethylbenzyl, p-pivaloyloxybenzyl, p-t-butoxycarbonyl benzyl, p-methylbenzyl, p-benzoyloxybenzyl, p-acetoxybenzyl, p-2-ethylhexanoylbenzoyl, p-ethoxycarbonylbenzyl, p-benzoylthiobenzyl, p-benzamidobenzyl, o-pivaloyloxybenzyl, m-pivaloyloxybenzyl, p-isopropoxybenzyl, p-t-butoxybenzyl, as well as the cyclic analogues thereof, 2,2-dimethyl-5-coumaranmethyl, 5-indanylmethyl, p-trimethylsilylbenzyl, 3,5-bis-t-butoxy-4-hydroxybenzyl; 2-thienylmethyl, 2-furylmethyl, 3-t-butyl-5-isothiazolmethyl, 6-pivaloyloxy-3-pyridazinylethyl, 5-phenylthio-1-tetrazolylmethyl, or the like (the use of the terms lower alkyl or lower alkoxy in this context means 1–4 carbon atoms chain); or phthalidyl; or phenylethyl, 2-(p-methylphenyl)ethyl, and the arylthioalkyl analogues, aryloxyalkyl wherein aryl is preferably a phenyl ring ahving 0–3 substituents preferably 0 or 1 substituents in the ortho or para positions and alkyl is 1–6 carbon atoms, e.g., (4-methoxy)-phenoxymethyl, phenoxymethyl, (4-chloro)phenoxymethyl, (4-nitro)phenoxymethyl, (4-benzyloxy)-phenoxymethyl, (4-methyl)phenoxymethyl, (4-benzyloxy)phenoxymethyl, (4-methyl)phenoxymethyl, (2-methoxy)phenoxymethyl, (1-phenoxy)ethyl, (4-amino)-phenoxymethyl, (4-methoxy)phenylthiomethyl, (4-chloro)phenylthiomethyl, phenylthioethyl; aryl wherein aryl is phenyl, 5-indanyl, or substituted phenyl having 0–3 substituents, preferably 0 or 1 substituent in the ortho or para position, e.g., (4-methyl)phenyl, (4-hydroxy)phenyl, (4-t-butyl)phenyl, p-nitrophenyl, 3,5-dinitrophenyl, or p-carboxyphenyl, the latter having either the free acid or the sodium salt form; aralkenyl wherein aryl is phenyl and alkenyl has 1–6 carbon atoms, such as 3-phenyl-2-propenyl; aralkoxyalkyl wherein aralkoxy is benzyloxy, and alkyl has 1–3 carbon atoms, such as benzyloxymethyl, (4-nitro)benzyloxymethyl, (4-chloro)benzyloxymethyl; alkylthioalkyl wherein the alkylthio portion has 1–10 and preferably 1–6 carbon atoms, but can be branched, straight or cyclic, and the alkyl portion has 1–6 carbon atoms, such as methylthioethyl, ethylthioethyl, cyclohexylthiomethyl, decylthiobutyl, methylthiopropyl, isopropylthioethyl, methylthiobutyl and the like.

In addition to the esters (and thio esters) listed above, amides are also embraced by the present invention, i.e., wherein X is the

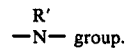
—N— group.

Representative of such amides are those wherein R' is selected from the group consisting of hydrogen, methyl, ethyl, phenyl, p-methoxyphenyl, benzyl, carboxymethyl, methylthioethyl, and heteroaryl; also embraced by —COXR$^4$ are anhydrides wherein R$^4$ is benzyloxycarbonyl, ethoxycarbonyl, benzoyl, and pivaloyl.

The most preferred —COXR$^4$ radicals of the present invention are those wherein (relative to Structure I above) X is oxygen, sulphur or NR' (R' is selected from the group consisting of hydrogen and lower alkyl); and R$^4$ is selected from the group consisting of: loweralkyl, lower alkenyl, such as methallyl, 3-methylbutenyl, 3-butenyl, and the like; methylthioethyl; benzyl and substituted benzyl such as p-t-butylbenzyl, m-phenoxybenzyl, p-pivaloyloxybenzyl, p-nitrobenzyl and the like; pivaloyloxymethyl, 3-phthalidyl and acetoxymethyl, propionyloxymethyl, acetylthiomethyl, pivaloylthiomethyl, allyl, 4-butenyl, 2-butenyl, 3-methyl-2-butenyl, phenacyl, acetoxyacetylmethyl, methoxymethyl, p-acetoxybenzyl, p-pivaloyloxybenzyl, p-isopropoxybenzyl, 5-indanylmethyl, 5-indanyl, benzyloxymethyl, ethylthioethyl, methylthiopropyl, methoxycarbonyloxymethyl, ethoxycarbonyloxymethyl, dimethylaminoacetoxymethyl, crotonolacton-3-yl, and acetamidomethyl.

Identification of R$^3$ and R$^2$

In the generic representation of the present invention, structure I (above), the radical R$^3$ is, in addition to hydrogen, (1.) acyl (generically the group —OR$^3$ is classifiable as an ester); or (2.) R$^3$ is selected from alkyl, aryl, aralkyl, and the like such that the group —OR$^3$ is classifiable as an ether. For the ester embodiments (1) R$^3$ is selected from the following definition of acyl radicals (p=1). In the so-called ether embodiments (2) of the present invention, R$^3$ is selected from the same acyl radicals wherein the carbonyl moiety,

or more generally,

is deleted (p=0); thus R$^3$ is selected from the following radicals wherein all symbolism is defined below. The radical R$^2$ of structure I is acyl (p=1) and is also defined below:

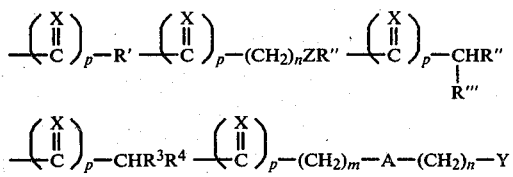

Thus, relative to the definition of $R^3$ and $R^2$, the acyl radical can, inter alia, be substituted or unsubstituted aliphatic, aromatic or heterocyclic, araliphatic or heterocyclylaliphatic carboxylic acid radical, a substituted or unsubstituted carbamyl radical or a carbothioic acid radical. One group of acyl radicals can be represented by the general formula:

wherein X is O or S and R" represents hydrogen; amino; substituted amino such as alkyl- and dialkyl-amino wherein the alkyl radical comprises 1 to about 6 carbon atoms; substituted or unsubstituted: straight or branched chain alkyl wherein the alkyl radical comprises 1 to about 6 carbon atoms; mercapto aryloxy, typically comprising 6 to 10 carbon atoms; alkenyl, or alkynyl groups typically comprising 2 to 6 carbon atoms; aryl such as phenyl; aralkyl such as benzyl; cycloalkyl, typically comprising 3 to 6 carbon atoms; or a heteroaryl or heteroaralkyl group (mono- and bicyclic) wherein the alkyl moiety typically comprises 1 to 3 carbon atoms and the heterocyclic ring comprises typically 4 to 10 atoms and the hetero atom or atoms are selected from O, N and S; such above-listed groups can be unsubstituted or can be substituted by radicals such as OH, SH, SR (R is lower alkyl or aryl such as phenyl), alkyl or alkoxy groups having 1 to about 6 carbon atoms, halo, such as Cl, Br, R and I, cyano, carboxy, sulfamino, carbamoyl, sulfonyl, azido, amino, substituted amino such as alkylamino including quaternary ammonium wherein the alkyl group comprises 1 to 6 carbon atoms, haloalkyl such as trifluoromethyl, carboxyalkyl, carbamoylalkyl, N-substituted carbamoylalkyl, wherein the alkyl moiety of the foregoing four radicals comprises 1 to about 6 carbon atoms, amidino, guanidino, N-substituted guanidino, guanidino lower alkyl and the like. Representative examples of such acyl groups that might be mentioned are those wherein R" is benzyl, p-hydroxybenzyl, 4-amino-4-carboxybutyl, methyl, cyanomethyl, 2-pentenyl, n-amyl, n-heptyl, ethyl 3- or 4-nitrobenzyl, phenethyl, β,β-diphenylethyl, methyldiphenylmethyl, triphenylmethyl, 2-methoxyphenyl, 2,6-dimethoxyphenyl, 2,4,6-trimethoxyphenyl, 3,5-dimethyl-4-isoxazolyl, 3-butyl-5-methyl-4-isoxazolyl, 5-methyl-3-phenyl-4-isoxazolyl, 3-(2-chlorophenyl)-5-methyl-4-isoxazolyl, 3-(2,6-dichlorophenyl)5-methyl-4-isoxazolyl, D-4-amino-4-carboxybutyl, D-4N-benzoylamino-4-carboxy-n-butyl, p-aminobenzyl, o-aminobenzyl, m-aminobenzyl, p-dimethylaminobenzyl, (3-pyridyl)methyl, 2-ethoxy-1-naphthyl, 3-carboxy-2-quinoxalinyl, 3-(2,6-dichlorophenyl)-5-(2-furyl)-4-isoxazolyl, 3-phenyl-4-isoxazolyl, 4-guanidinomethylphenyl, 4-guanidinomethylbenzyl, 4-guanidinobenzyl, 4-guanidinophenyl, 2,6-dimethoxy-4-guanidino, o-sulfobenzyl, p-carboxymethylbenzyl, p-carbamoylmethylbenzyl, m-fluorobenzyl, m-bromobenzyl, p-chlorobenzyl, p-methoxybenzyl, 1-naphthylmethyl, 3-isothiazolylmethyl, 4-isothiazolylmethyl, 5-isothiazolylmethyl, guanylthiomethyl, 4-pyridylmethyl, 5-isoxazolylmethyl, 4-methoxy-5-isoxazolylmethyl, 4-methyl-5-isoxazolylmethyl, 1-imidazolylmethyl, 2-benzofuranylmethyl, 2-indolylmethyl, 2-phenylvinyl, 2-phenylethynyl, 1-aminocyclohexyl, 2- and 3-thienylaminomethyl, 2-(5-nitrofuranyl)vinyl, phenyl, o-methoxyphenyl, o-chlorophenyl, o-phenylphenyl, p-aminomethylbenzyl, 1-(5-cyanotriazolyl)methyl, difluoromethyl, dichloromethyl, dibromomethyl, 1-(3-methylimidazolyl)methyl, 2- or 3-(5-carboxymethylthienyl)methyl, 2- or 3-(4-carbamoylthienyl)methyl, 2- or 3-(5-methylthienyl)methyl, 2- or 3-(methoxythienyl)methyl, 2- or 3-(4-chlorothienyl)methyl, 2- or 3-(5-sulfothienyl)methyl, 2- or 3-(5-carboxythienyl)methyl, 3-(1,2,5-thiadiazolyl)methyl, 3-(4-methxoy-1,2,5-thiadiazolyl)methyl, 2-furylmethyl, 2-(5-nitrofuryl)methyl, 3-furylmethyl, 2-thienylmethyl, 3-thienylmethyl, tetrazolylmethyl, benzamidinomethyl and cyclohexylamidinomethyl.

The acyl group can also be a radical of the formula:

wherein X is O or S and n is 0–4, Z represents oxygen, sulfur, carbonyl or nitrogen and R" is defined as above. Representative members of the substituent

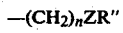

that might be mentioned are allylthiomethyl, phenylthiomethyl, butylmercaptomethyl, α-chlorocrotylmercaptomethyl, phenoxymethyl, phenoxyethyl, phenoxybutyl, phenoxybenzyl, diphenoxymethyl, dimethylmethoxyethyl, dimethylbutoxymethyl, dimethylphenoxymethyl, 4-guanidinophenoxymethyl, 4-pyridylthiomethyl, p-(carboxymethyl)phenoxymethyl, p-(carboxymethylphenylthiomethyl, 2-thiazolylthiomethyl, p-(sulfo)phenoxymethyl, p-(carboxymethyl)phenylthiomethyl, 2-pyrimidinylthiomethyl, phenethylthiomethyl, 1-(5,6,7,8-tetrahydronaphthyl)oxomethyl, N-methyl-4-pyridylthio, benzyloxy, methoxy, ethoxy, phenoxy, phenylthio, amino, methylamino, dimethylamino, pyridinium methyl, trimethylammoniummethyl, cyanomethylthiomethyl, trifluoromethylthiomethyl, 4-pyridylethyl, 4-pyridylpropyl, 4-pyridylbutyl, 3-imidazolylethyl, 3-imidazolylpropyl, 3-imidazolylbutyl, 1-pyrroloethyl, 1-pyrrolopropyl, and 1-pyrrolobutyl.

Alternatively, the acyl group can be a radical of the formula:

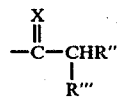

wherein R" is defined as above and R'" is a radical such as amino, hydroxy, azido, carbamoyl, guanidino, amidino, acyloxy, halo, such as Cl, F. Br, I, sulfamino, tetrazolyl, sulfo, carboxy, carbalkoxy, phosphono and the like. Representative members of the substituent

that might be mentioned are α-aminobenzyl, α-amino-(2-thienyl)methyl, α-(methylamino)benzyl, α-aminomethylmercaptopropyl, α-amino-3- or 4-chlorobenzyl, α-amino-3- or 4-hydroxybenzyl, α-amino-2,4-dichlorobenzyl, α-amino-3,4-dichlorobenzyl, D(−)-α-hydroxybenzyl, α-carboxybenzyl, α-amino-(3-thienyl)methyl D(−)-α-amino-3-chloro-4-hydroxybenzyl, α-amino(cyclohexyl)methyl, α-(5-tetrazolyl)benzyl, 2-thienyl-carboxymethyl, 3-thienyl-carboxymethyl, 2-furylcarboxymethyl, 3-furyl-carboxymethyl, α-sulfaminobenzyl, 3-thienyl-sulfaminomethyl, α-(N-methylsulfonamino)-benzyl D(−)-2-thienyl-guanidinomethyl, D(−)-α-guanidinobenzyl α-guanylureidobenzyl, α-hydroxybenzyl, α-azidobenzyl, α-fluorobenzyl, 4-(5-methxoy-1,3-oxadizolyl)-aminomethyl, 4-(5-methoxy-1,3-oxadiazolyl)-hydroxymethyl, 4-(5-methoxy-1,3-sulfadiazolyl)-hydroxymethyl, 4-(5-chlorothienyl-)aminomethyl, 2-(5-chlorothienyl)-hydroxymethyl, 2-(5-chlorothienyl)-carboxy-methyl, 3-(1,2-thiazolyl)-aminomethyl, 3-(1,2-thiazolyl)-hydroxymethyl, 3-(1,2-thiazolyl)carboxymethyl, 2-(1,4-thiazolyl)-aminomethyl, 2-(1,4-thiazolyl)-hydroxymethyl, 2-(1,4-thiazolyl)carboxymethyl, 2-benzothienylaminomethyl, 2-benzothienylhydroxymethyl, 2-benzothienylcarboxymethyl, α-sulfobenzyl, α-phosphonobenzyl, α-diethylphosphono, and α-monoethylphosphono. Further acyl radicals of interest in this class when X=oxygen are:

wherein R$^{3'}$ and R$^{4'}$ are as defined below. R$^{3'}$ represents hydrogen, halo, such as chloro, fluoro, bromo, iodo, amino, guanidino, phosphono, hydroxy, tetrazolyl, carboxy, sulfo, or sulfamino and R$^{4'}$ represents phenyl, substituted phenyl, a mono- or bicyclic heterocyclyl containing one or more oxygen, sulfur or nitrogen atoms in the ring, such as furyl, quinoxalyl, thienyl, quinolyl, quinazolyl, thiazolyl, siothiazolyl, tetrazolyl, oxadiazolyl, thiadiazolyl and and the like substitued heterocycles, phenylthio, phenyloxy lower alkyl of 1–6 carbon atoms, heterocyclic or substituted heterocyclic thio groups; or cyano. The substituents on the moieties, R$^{3'}$ and R$^{4'}$, can be halo, carboxymethyl, guanidino, guanidinomethyl, carboxamidomethyl, aminomethyl, nitro, methoxy or methyl. When R$^{3'}$ is selected from the group consisting of hydrogen, hydroxy, amino or carboxy and R$^{4'}$ is selected from the group consisting of phenyl, or a 5- or 6-membered heterocyclic ring having one or two sulfur, oxygen or nitrogen hetero atom such as tetrazolyl, thienyl, furyl and phenyl, the following acyl radicals are representative: phenylacetyl 3-bromophenylacetyl, p-aminomethylphenylacetyl, 4-carboxymethylphenylacetyl, 4-carboxyamidomethylphenylacetyl, 2-furylacetyl, 5-nitro-2-furylacetyl, 3-furylacetyl, 2-thienylacetyl, 5-chloro-2-thienylacetyl, 5-methoxy-2-thienylacetyl, α-guanidino-2-thienylacetyl, 3-thienylacetyl, 2-(4-methylthienyl)acetyl, 3-isothiazolylacetyl, 4-methoxy-3-isothiazolylacetyl, 4-isothiazolylacetyl, 3-methyl-4-isothiazolylacetyl, 5-isothiazolylacetyl, 3-chloro-5-isothiazolylacetyl, 3-methyl-1,2,5-oxadiazolylacetyl, 1,2,5-thiadiazolyl-4-acetyl, 3-methyl-1,2,5-thiadiazolylacetyl, 3-chloro-1,2,5-thiadiazolylacetyl, 3-methoxy-1,2,5-thiadiazolylacetyl, phenylthioacetyl, 4-pyridylthioacetyl, cyanoacetyl, 1-tetrazolylacetyl, α-fluorophenylacetyl, D-phenylglycyl, 4-hydroxy-D-phenylglycyl, 2-thienylglycyl, 3-thienylglycyl, phenylmalonyl, 3-chlorophenylmalonyl, 2-thienylmalonyl, 3-thienylmalonyl, α-phosphonophenylacetyl, α-amino cyclohexadienylacetyl, α-sulfaminophenylacetyl, α-hydroxyphenylacetyl, α-tetrazolylphenylacetyl and α-sulfophenylacetyl.

The acyl radical may also be selected from sulphur (1) and phosphorous (2) radicals:

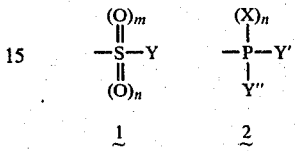

wherein with respect to 1, m and n are integers selected from 0 or 1 and Y=O$^{\ominus}$M$^{\oplus}$, —N(R″)$_2$, and R″; wherein M$^{\oplus}$ is selected from hydrogen, alkali metal cations and organic bases; and R″ is as defined above, e.g., alkyl, alkenyl, aryl and heteroaryl. With respect to 2 X=O or S; n=0 or 1; and Y′ and Y″ are selected from the group consisting of O$^{\ominus}$M$^{\oplus}$, —N(R″)$_2$, R″ and ZR″ wherein all symbolism is as defined above, e.g., R″ and ZR″ are representatively: alkyl, alkenyl, aryl, heteroaryloxy, Y′ and Y″, including R″ moieties, can be joined together to form cyclic ester, ester- amide and amide functions. Illustrative examples of radicals 1 are: methylsulphonyl, p-nitrophenylsulphonyl, p-chlorophenylsulphinyl, o-nitrophenylsulphenyl, sulfamoyl, dimethylsulphamoyl, and sulpho; illustrative examples of radicals 2 are: dimethoxyphosphino, dibenzyloxyphosphino, dihydroxyphosphino, dimethoxyphosphinyl, dimethoxyphosphinothioyl, dibenzyloxyphosphinyl, and dihydroxyphosphinyl.

An acyl class of particular interest is those acyl radicals which are selected from the group consisting of conventionally known N-acyl blocking or protective groups such as carbobenzyloxy, ring-substituted carbobenzyloxy such as o- and p-nitrocarbobenzyloxy, p-methoxycarbobenzyloxy, chloroacetyl, bromoacetyl, phenylacetyl, t-butoxycarbonyl, trifluoroacetyl, bromoethoxycarbonyl, 9-fluoroenylmethoxycarbonyl, dichloroacetyl, o-nitrophenylsulfenyl, 2,2,2-trichloroethoxycarbonyl, bromo-t-butoxycarbonyl, phenoxyacetyl; non-acyl protective groups such as trilower alkyl silyl, for example, trimethylsilyl and t-butyldimethyl are also of interest.

The following radicals, according to the foregoing definition of acyl, are preferred: formyl, propionyl, butyryl, chloroacetyl, methoxyacetyl, aminoacetyl, methoxycarbonyl, ethoxycarbonyl, methylcarbamoyl, ethylcarbamoyl, phenylthiocarbonyl, 3-aminopropionyl, 4-aminobutyryl, N-methylaminoacetyl, N,N-dimethylaminoacetyl, N,N,N-trimethylaminoacetyl, 3-(N,N-dimethyl)aminopropionyl, 3-(N,N,N-trimethyl)aminopropionyl, N,N,N-triethylaminoacetyl, pyridiniumacetyl, guanidinoacetyl, 3-guanidinopropionyl, N$^3$-methylguanidinopionyl, hydroxyacetyl, 3-hydroxypropionyl, acryloyl, propynoyl, malonyl, phenoxycarbonyl, amidinoacetyl, acetamidinoacetyl, amidinopropionyl, acetamidinopropionyl, guanylureidoacetyl, guanylcarbamoyl, carboxymethylaminoacetyl, sulfoacetylaminoacetyl, phosphonoacetylaminoacetyl, N$^3$- dimethylaminoacetamidinopropionyl, ureidocarbonyl, dimethylaminoguanylthioacetyl, 3-(1-methyl-4-pyridinium)propionyl, 3-(5-aminoimidazol-1-yl)propionyl, 3-methyl-1-imidazoliumacetyl, 3-sydnonylacetyl, o-aminomethylbenzoyl, o-aminobenzoyl,

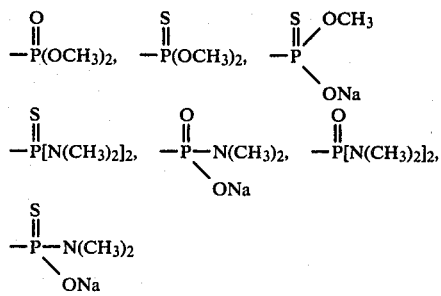

An especially preferred class of acyl radicals are terminally substituted acyls wherein the substituent is a basic group such as substituted and unsubstituted: amino, amidino, guanidino, guanyl and nitrogen-containing mono- and bicyclic heterocycles (aromatic and non-aromatic) wherein the hetero atom or atoms, in addition to nitrogen, are selected from oxygen and sulphur. Such preferred substituted acyls may be represented by the following formula:

$$-\underset{\|}{\overset{O}{C}}(CH_2)_m-A-(CH_2)_n-Y$$

wherein m, and n are integers selected from 0 to 5; A is O, NR' (R' is hydrogen or loweralkyl having 1-6 carbon atoms), S or A represents a single bond; and Y is selected from the following group:
(1) amino or substituted amino:
 $-N(R)_2$ and $-N^+(R)_3$ wherein the values for R are independently selected from: hydrogen; N(R')₂ (R' is hydrogen or loweralkyl having 1-6 carbon atoms); loweralkyl and loweralkoxyl having from 1 to 6 carbon atoms; loweralkoxyloweralkyl wherein the alkoxyl moiety comprises 1 to 6 carbon atoms and the alkyl moiety comprises 2-6 carbon atoms; cycloalkyl and cycloalkylalkyl wherein the cycloalkyl moiety comprises 3-6 carbon atoms and the alkyl moiety comprises 1-3 carbon atoms, two R groups may be joined together with the N atom to which they are attached to form a ring having 3-6 atoms.
(2) amidino and substituted amidino:

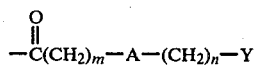

wherein the value of R is independently selected from the group consisting of: hydrogen; N(R')₂ (R' is hydrogen or loweralkyl having 1-6 carbon atoms); loweralkyl and loweralkoxyl having from 1 to 6 carbon atoms, loweralkoxyloweralkyl wherein the alkoxyl moiety comprises 1 to 6 carbon atoms and the alkyl moiety comprises 2 to 6 carbon atoms (when the loweralkoxyloweralkyl radical is attached to carbon the alkyl moiety comprises 1 to 6 carbon atoms); cycloalkyl and cycloalkylalkyl wherein the alkyl moiety comprises 1 to 3 carbon atoms; two R groups may be joined together with the atoms to which they are attached to form a ring having 3 to 6 atoms;
(3) guanidino and substituted guanidino:

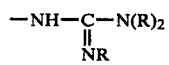

wherein R is as defined in (2) (above).
(4) guanyl and substituted guanyl:

wherein R is as defined in (2) (above).
(5) nitrogen-containing mono- and bicyclic heterocyclyls (aromatic and non-aromatic) having 4 to 10 nuclear atoms wherein the hetero atom or atoms, in addition to nitrogen, are selected from oxygen and sulphur. Such heterocyclyls are representatively illustrated by the following list of radicals (R' is H or loweralkyl having 1-6 carbon atoms):

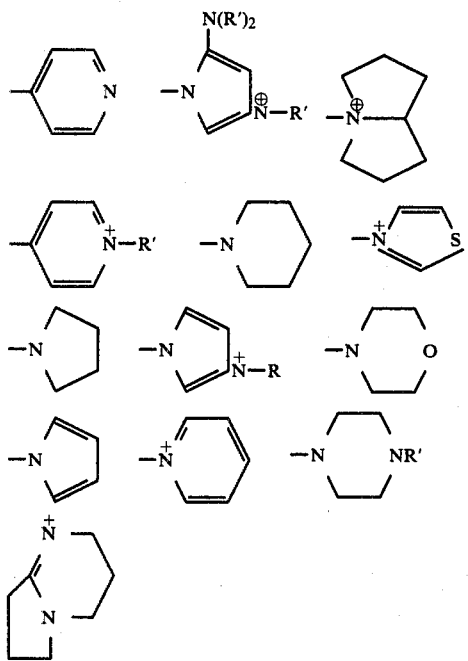

The following specific acyl radicals falling within this class are additionally representative and are preferred:

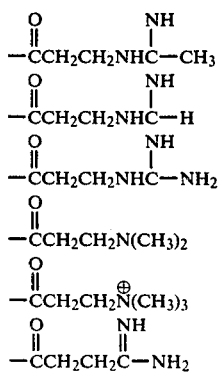

-continued

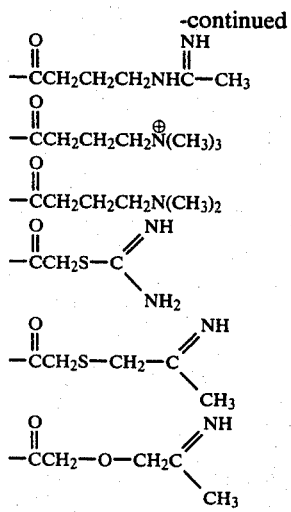

However, it is to be understood that any acyl radical may be employed in the practice of the invention and is to be considered within the scope of the invention.

Preparation of Starting Materials Ia, Ib, and Ic

The above-described starting materials are conveniently prepared from an N-protected thienamycin species such as an N-acylated thienamycin (1)

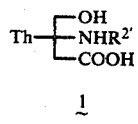

wherein $R^{2'}$ is an easily removable blocking group such as: carbobenzyloxy, ring-substituted carbobenzyloxy such as o- and p-nitrocarbobenzyloxy, p-methoxycarbobenzyloxy, chloroacetyl, bromoacetyl, phenylacetyl, t-butoxycarbonyl trifluoroacetyl, bromoethoxycarbonyl, 9-fluoroenylmethoxycarbonyl, dichloroacetyl, o-nitrophenylsulfenyl, 2,2,2-trichloroethoxycarbonyl, bromo-t-butoxycarbonyl, phenoxyacetyl; non-acyl protective groups such as triloweralkylsilyl, for example, trimethylsilyl, and t-butyldimethylsilyl are also of interest. The most preferred N-blocking groups are the substituted and unsubstituted carbobenzyloxy radical:

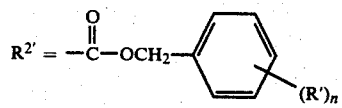

wherein n is 0–2 (n=0, R'=hydrogen) and R' is lower alkoxy or nitro; and bromo-t-butoxycarbonyl.

The ultimate N-deblocking procedure for the preparation of Ia, Ib or Ic is accomplished by any of a variety of well-known procedures which include hydrolysis or hydrogenation; when hydrogenation is employed suitable conditions involve a solvent such as a loweralkanoyl in the presence of a hydrogenation catalyst such as palladium, platinum or oxides thereof.

The N-acylated intermediate (1, above) is prepared by treating thienamycin (II) with an acylating agent, for example, an acyl halide or acyl anhydride such as an aliphatic, aromatic, heterocyclic, araliphatic or heterocyclic aliphatic carboxylic acid halide or anhydride. Other acylating agents may also be employed, for example, mixed carboxylic acid anhydrides and particularly lower alkyl esters of mixed carboxylic-carbonic anhydrides; also, carboxylic acids in the presence of a carbodiimide such as 1,3-dicyclohexylcarbodiimide, and an activated ester of a carboxylic acid such as the p-nitrophenyl ester. Such N-acylated thienamycin starting materials are fully described in the above-cited, incorporated by reference, co-pending U.S. patent application Ser. No. 733,653, filed Oct. 18, 1976, now abandoned.

The acylation reaction may be conducted at a temperature in the range of from about −20° to about 100° C., but is preferably conducted at a temperature in the range of from −9° C. to 25° C. Any solvent in which the reactants are soluble and substantially inert may be employed, for example polar solvents such as water, alcohols and polar organic solvents in general such as dimethylformamide (DMF), hexamethyl phsophoramide (HMPA), acetone, dioxane tetrahydrofuran (THF), acetonitrile, heterocyclic amines such as pyridine, ethylacetate, aqueous mixtures of the above, as well as halogenated solvents such as methylene chloride and chloroform. The reaction is conducted for a period of time of from about five minutes to a maximum of three hours, but in general, a reaction time of about 0.5 to about one hour is sufficient. The following equation illustrates this process employing a carboxylic acid halide; however, it is to be understood that by substituting a carboxylic acid anhydride or other functionally equivalent acylating agent similar products may be obtained.

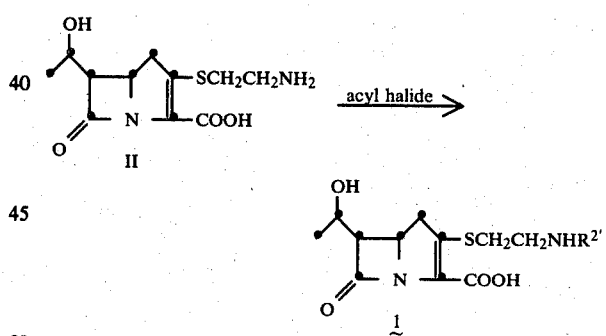

Generally when the above-described acylating reaction employs an acid halide (suitable halides are chloro, iodo, or bromo) or anhydride the reaction is conducted in water or an aqueous mixture of a polar organic solvent such as acetone, dioxane, THF, DMF, acetonitrile or the like in the presence of a suitable acceptor base such as NaHCO₃, MgO, NaOH, K₂HPO₄ and the like.

In carrying out the reactions described herein, it is generally not necessary to protect the 2-carboxy group or the 1'-hydroxy group; however, in cases where the acylating reagent is exceedingly water sensitive it is sometimes advantageous to perform the acylation in a non aqueous solvent system. Triorganosilyl (or tin) derivatives of thienamycin proceed rapidly to give the tris-triorganosilyl derivative, for example tris-trimethylsilyl thienamycin Th(TMS)₃:

Such derivatives, which are readily soluble in organic solvents, are conveniently prepared by treating thienamycin with an excess of hexamethyldisilazane and a stoichiometric amount of trimethylchlorosilane at 25° C., with vigorous stirring under a $N_2$ atmosphere. The resulting $NH_4Cl$ is removed by centrifugation and the solvent is removed by evaporation to provide the desired silyl derivative.

The intermediate starting materials Ib are prepared according to the following scheme; however, it should be noted that direct esterification, without protection of the amino group, is also possible.

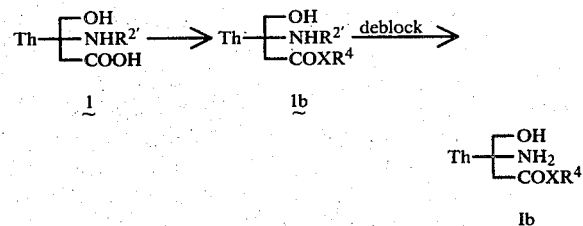

wherein all symbolism is as previously defined.

In general, the transformation (1→Ib) is accomplished by conventional procedures known in the art. Such procedures include:

(1) Reaction of 1 (or II, thienamycin) with a diazoalkane such as diazomethane, phenyldiazomethane, diphenyldiazomethane, and the like, in a solvent such as dioxane, ethylacetate, acetonitrile and the like at a temperature of from 0° C. to reflux for from a few minutes to 2 hours.

(2) Reaction of an alkali metal salt of 1 with an activated alkyl halide such as methyliodide, benzyl bromide, or m-phenoxybenzyl bromide, p-t-butylbenzyl bromide, pivaloyloxymethyl chloride, and the like. Suitable reaction conditions include solvents such as hexamethylphosphoramide and the like at a temperature of from 0° C. to 60° C. for from a few minutes to 4 hours.

(3) Reaction of 1 with an alcohol such as methanol, ethanol, benzyl alcohol, and the like. This reaction may be conducted in the presence of a carbodiimide condensing agent such as dicyclohexylcarbodiimide or the like. Suitable solvent, at a temperature of from 0° C. to reflux for from 15 minutes to 18 hours, include $CHCl_3$, $CH_3CH$, $CH_2Cl_2$ and the like.

(4) Reaction of an N-acylated acid anhydride of 1 prepared by reacting the free acid 1 with an acid chloride such as ethylchloroformate, benzylchloroformate and the like, with an alcohol such as those listed in (3) under the same conditions of reaction as given above for (3). The anhydride is prepared by reacting 1 and the acid chloride in a solvent such as tetrahydrofuran (THF), $CH_2Cl_2$ and the like at a temperature of from 25° C., to reflux for from 15 minutes to 10 hours.

(5) Reaction of labile esters of 1 such as the trimethylsilyl ester, dimethyl-t-butylsilyl ester or the like with $R^4X'$ wherein X' is halogen such as bromo and chloro and $R^4$ is as defined, in a solvent such as THF, $CH_2Cl_2$ and the like at a temperature of from 0° C. to reflux for from 15 minutes to 16 hours. For example according to the following scheme:

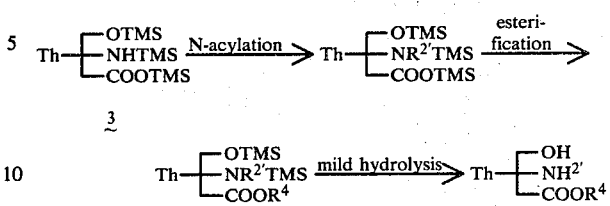

wherein TMS is triorganosilyl such as trimethylsilyl and all other symbolism is as previously defined.

Amides are most conveniently prepared by reacting the acid anhydride of Ib (X=O, R=acyl) with ammonia or with the amine of choide, e.g., the alkyl-, dialkyl-, aralkyl- or heterocyclic amines listed above.

The above-recited schemes of esterification are well known in the related bicyclic β-lactam antibiotic art and indeed in all of general organic synthesis and it is to be noted that there is no undue criticality of reaction parameters in the preparation of the N-acylated, carboxyl derivatives Ib useful as starting materials in the practice of the present invention.

Starting materials Ia and Ic are conveniently prepared by any of a variety of well-known esterification or etherification reactions upon the secondary alcoholic group of Ib Such procedures include:

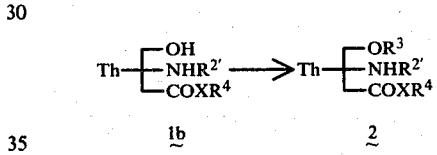

(1) For the preparation of ether embodiments of the present invention, the acid catalyzed reaction of Ib with a diazoalkane such as diazomethane, phenyldiazomethane, diphenyldiazomethane and the like in an inert solvent such as dioxane, tetrahydrofuran (THF), halohydrocarbons such as $CH_2Cl_2$, ethylacetate and the like in the presence of a catalytic amount of a strong acid or Lewis acid such as toluenesulfonic acid, trifluoroacetic acid, fluoboric acid, boron trifluoride and the like at a temperature of from −78° C. to 25° C. for from a few minutes to 2 hours.

(2) For the preparation of ether embodiments of the present invention, the reaction of Ib with an alkylating agent such as active halides, for example methyliodide, benzylbromide, m-phenoxybenzylbromide and the like; alkylsulphonates such as dimethylsulphate, diethylsulphate, methylfluorosulphonate and the like in the presence of a strong base capable of forming the alcoholate anion of Ib. Suitable bases include alkali and alkaline earth metal oxides and hydrous oxides, alkali metal alkoxides such as potassium, tertiarybutoxide, tertiary amines such as triethylamine, alkali metal alkyls and aryls such as phenyllithium, and alkali metal amides such as sodium amide. Suitable solvents include any inert anhydrous solvent such as t-butanol, dimethylformamide (DMF), THF, hexamethylphosphoramide (HMPA) dioxane and the like at a temperature of from −78° C. to 25° C., for from a few minutes to 4 hours.

(3) For the preparation of ester embodiments, of the present invention, the reaction of Ib with any of the above-listed acyl radicals in their acid form. This reaction may be conducted in the presence of a carbodiimide condensing agent such as dicyclohexylcarbodiimide or the like. Suitable solvents include any inert solvent such as CHCl₃, CH₂Cl₂, DMF, HMPA, acetone, dioxane and the like at a temperature of from 0° C. to 60° C. for from 15 minutes to 12 hours.

(4) For the preparation of ester embodiments of the present invention, the reaction of 1b with an acyl halide or an acid anhydride, wherein the acyl moiety is described above. Generally, when the above-described acylating reaction employs an acid halide (suitable halides are chloro, iodo, or bromo or acid anhydride) the reaction is conducted in an anhydrous organic solvent such as acetone, dioxane, methylenechloride chloroform, DMF, or the like in the presence of a suitable acceptor base such as NaHCO₃, MgO, triethylene, pyridine, and the like at a temperature of from 0° C. to 40° C. for from 1 to 4 hours.

Suitable acyl halides and anhydrides include: acetic anhydride, bromoacetic anhydride, propionic anhydride, benzoylchloride, phenylacetyl, chloride azidoacetyl chloride, 2-thienylacetyl chloride, 2-, 3-and 4-nicotinyl chloride, p-nitrobenzoyl chloride, 2,6-dimethoxybenzoyl chloride, 4-guanidinophenylacetyl chloride, hydrochloride, methanesulfonyl chloride, dibenzylphosphorochloridate, dimethylthiophosphorochloridate, 2-furoyl, ethyl carbonic anhydride, methylchloroformate, bis(p-nitrobenzyl)phosphorochloridate and the like.

(5) For the preparation of ester embodiments of the present invention, the reaction of 1b with a suitably substituted ketene or isocyanate such as ketene, dimethyl ketene, methylisocyanate, methylisothiocyanate, chlorosulfonyl isocyanae and the like. Suitable solvents include dioxane, tetrahydrofuran, chloroform and the like at a temperature of from −70° C. to 60° C. for from 15 minutes to 18 hours.

The intermediate 2 is then N-deblocked as described above to provide starting material Ic. From Ic, Ia is prepared by deblocking the carboxyl group:

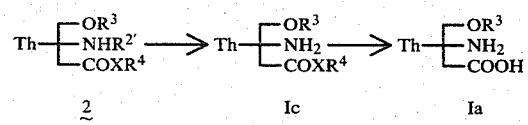

Starting material Ia is conveniently and preferably obtained when X is oxygen and R⁴ is a readily removable carboxyl protecting or blocking group (see above). Starting material Ia is prepared by deblocking according to any of a variety of well-known procedures which include hydrolysis and hydrogenation. When the preferred carboxyl-blocking groups are employed (below), the preferred deblocking procedure is hydrogenation, wherein the intermediate species (Ic or 2) in a solvent such as a lower alkanoyl, is hydrogenated in the presence of a hydrogenation catalyst such as palladium, platinum or oxides thereof.

In this connection, it is noted that suitable "blocking groups" R⁴ include the sub-generic groups defined above as aralkyl, haloalkyl, alkanoyloxyalkyl, alkoxyalkyl, alkenyl, substituted alkyl, or aralkoxyalkyl, and also including alkylsilyl, wherein alkyl has 1–10 carbon atoms. For example, suitable "blocking groups" R⁴ include benzyl, phenacyl, p-nitrobenzyl, methoxymethyl, trichloroethyl, trimethylsilyl, tributyltin, p-methoxybenzyl, benzhydryl. These blocking groups are preferred since they are generally recognized easily-removable blocking groups in cephalosporin and penicillin art.

The preferred carboxyl blocking groups, are benzyl and substituted benzyl:

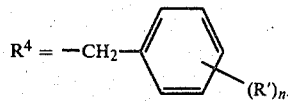

wherein n is 0-2 (n=O, R'=H) and R' is loweralkoxyl or nitro.

Normally, the final step in the preparation of the compounds of the present invention is the above described N-acylation reaction, III→I. This N-acylation is exactly as described for the establishment of R²' (structure 1, above) except that R²' is generically the above described acyl radical R². Also, the establishment of R³, —COXR⁴ or R³ and —COXR⁴ may be effected after the establishment of radicals R¹ and R² on the amino nitrogen of I to obtain further derivatized embodiments of I; such derivatizations are accomplished exactly as described for the preparation of Ia, Ib, and Ic, above.

The products of this invention (I) form a wide variety of pharmacologically acceptable salts with inorganic and organic bases; these include, for example, metal salts derived from alkali or alkaline earth metal hydroxides, carbonates or bicarbonates and salts derived from primary, secondary or tertiray amines such as monoalkylamines, dialkylamines, trialkylamines, lower alkanolamines, di-loweralkanolamines, lower alkylenediamines, N,N-diaralkyl lower alkylenediamines, aralkylamines, amino substitued lower alkanols, N,N-di-lower alkylamino substituted lower alkanols, amino-, polyamino- and guanidino-substituted lower alkanoic acids and nitrogen-containing heterocyclic amines. Representative examples include salts derived from sodium hydroxide, sodium carbonate, sodium bicarbonate, potassium carbonate, potassium hydroxide, calcium carbonate, trimethylamine, triethylamine, piperidine, morpholine, quinine, lysine, protamine, arginine, procaine, ethanolamine, morphine, benzylamine, ethylenediamine, N,N'-dibenzylethylenediamine, diethanolamine, piperazine, dimethylaminoethanol, 2-amino-2-methyl-1-propanol, theophylline, N-methylglucamine and the like. Acid addition salts, e.g, with hydrochloric hydrobromic, sulfuric, nitric, toluene-p-sulphonic and methane sulphonic acids may also be employed, in such instances where the acyl radial contains a basic group.

The salts can be mono-salts such as the monosodium salt obtained by treating one equivalent of sodium hydroxide with one equivalent of the product (I), also mixed di-salts. Such salts may be obtained by treating one equivalent of a base having a divalent cation, such as calcium hydroxide, with one equivalent of the product (I). The salts of this invention are pharmacologically acceptable nontoxic derivatives which can be used as the active ingredient in suitable unit-dosage pharmaceutical forms. Also, they may be combined with other drugs to provide compositions having a broad spectrum of activity.

The novel thienamycin derivatives of the present invention are valuable antimicrobial substances which are active against various gram-positive and gram-negative pathogens. Thus, the free acid and especially the salts thereof such as amine and metal salts, particularly the alkali metal and alkaline earth metal salts, are useful bactericides and can be used for removing susceptible pathogens from dental and medical equipment, for separating microorganisms, and for therapeutic use in humans and animals. For this latter purpose pharmacologically acceptable salts with inorganic and organic bases such as those known in the art and used for the administration of penicillins and cephalosporins can be utilized. For example, salts such as alkali metal and alkaline earth metal salts, and primary, secondary and tertiary amine salts can be used for this purpose. These salts can be combined with pharmaceutically acceptable liquid and solid vehicles to form suitable dosage unit forms such as pills, tablets, capsules suppositories, syrups, elixirs and the like which can be prepared in accordance with procedures well known in this art.

The novel compounds are valuable antibiotics active against various gram-positive and gram-negative bacteria, and accordingly, find utility in human and veterinary medicine. The compounds of this invention can therefore be used as antibacterial drugs for treating infections caused by gram-positive or gram-negative bacteria, for example against *Staphylococcus aureus, Escherichia coli, Klebsiella pneumoniae, Bacillus substilis, Salmonella typhosa,* Pseudomonas and *Bacterium proteus.* the antibacterials of the invention may further be utilized as additives to animal feedingstuffs, for preserving foodstuffs and disinfectants. For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example in waterbased paints and in the white water of paper mills to inhibit the growth of harmful bacteria.

The products of this invention may be used alone or in combination as an active ingredient in any one of a variety of pharmaceutical preparations. These antibiotics and their corresponding salts may be employed in capsule form or as tablets, powders or liquid solutions or as suspensions or elixirs. They may be administered orally, intraveneously or intramuscularly.

The compositions are preferably presented in a form suitable for absorption by the gastro-intestinal tract. Tablets and capsules for oral administration may be in unit dose presentation form, and may contain conventional excipients such as binding agents, for example, syrup, acacia, gelatin, sorbitol, tragacanth, or polyvinylpyrrolidone; fillers for example, lactose, sugar, maize-starch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspension, solution, emulsions, syrups, elixirs, etc. or may be presented as a dry product, for reconstitution with water or other suitable vehicles before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminum stearate gel or hydrogenated edible oils, for example almond oil, fractionated coconut oil, oily esters, propylene glycol, or ethyl alcohol; preservatives, for example methyl or propyl p-hydroxybenzoates or sorbic acid. Suppositories will contain conventional suppository bases, e.g. cocoa butter or other glyceride.

Compositions for injection may be presented in unit dose form in ampulses, or in multidose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form for reconstitution with a suitable vehicle, e.g. sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semi-solid form, or may be used as drops etc. Topical applications may be formulated in hydrophobic or hydrophilic bases as ointments, creams, lotions, paints, powders, etc.

Also, in addition to a carrier, the instant compositions may include other ingredients such as stabilizers, binders, antioxidants, preservatives, lubricators, suspending agents, viscosity agents or flavoring agents and the like. In addition, there may also be included in the composition other active ingredients to provide a broader spectrum of antibiotic activity.

For veterinary medicine the composition may, for example, be formulated as an intramammary preparation in either long acting or quick-release bases.

The dosage to be administered depends to a large extent upon the condition of the subject being treated and the weight of the host, the route and frequency of administration, the parenteral route being preferred for generalized infections and the oral route for intestinal infections. In general, a daily oral dosage consists of from about 15 to about 600 mg. of active ingredient per kg. of body weight of the subject in one or more applications per day. A preferred daily dosage for adult humans lies in the range of from about 80 to 120 mg. of active ingredient per kg. of body weight.

The instant compositions may be administered in several unit dosage forms as, for example, in solid or liquid orally ingestible dosage form. The compositions per unit dosage, whether liquid or solid may contain from 0.1% to 99% of active material, the preferred range being from about 10–60%. The composition will generally contain from about 15 mg. to about 1500 mg. of the active ingredient; however, in general, it is preferable to employ a dosage amount in the range of from about 250 mg. to 1000 mg. In parenteral administration the unit dosage is usually the pure compound in a slightly acidified sterile water solution or in the form of a soluble powder intended for solution.

The following examples, illustrate due do not limit the product, process, compositional or method of treatment aspects of the present invention.

EXAMPLE 1

N-Ethyl thienamycin

Thienamycin (120 mg) is dissolved in a mixture of 7 ml of 0.1 N pH 7 phosphate buffer and 3 ml of acetonitrile. The solution is adjusted to pH 9 by the addition of 1 N sodium hydroxide solution. Ethyl fluorosulfonate (0.5 ml) is added dropwise during 8 minutes while the pH is maintained by an automatic titrator. At the end of the reaction the mixture is adjusted to pH 7, diluted with 20 ml of water and then rapidly concentrated under reduced pressure to 10 ml. The dilution and concentration are repeated to further lower the acetonitrile content, then the solution is chromatographed on a column (2 cm×51 cm) of XAD-2 resin. The column is eluted with water taking 27 ml fractions. Thienamycin is recovered in fractions 18–30. The combined product fractions are concentrated to 10 ml and freeze dried yielding 14 mg (12%) of N-ethyl thienamycin. The 100 MHz NMR spectrum shows NCH$_2$C$\underline{H}_3$ triplet at 1.3δ superimposed on the C$\underline{H}_3$CHOH side chain doublet of equal intensity. The mass spectrum after silylation shows a molecular ion at m/e 444 corresponding to the disilyl derivative of N-ethyl thienamycin.

EXAMPLE 2

Preparation of N-Methyl Thienamycin

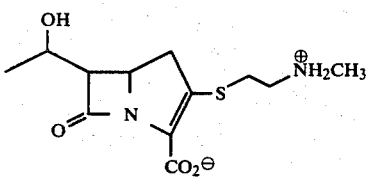

N-thioformyl thienamycin (80 mg) is dissolved in pH 7 0.1 N phosphate buffer (8 ml) and cooled in an ice bath. Deactivated Raney Nickel (Raney Nickel refluxed 1 hr. in acetone, 500 mg) suspended in ethyl acetate is then added to the magnetically stirred solution. The mixture is stirred 3 min and the catalyst separated from the solution. The product solution is chromatographed on Dowex 50-X4 (Na+cycle,200–400 mesh, 53 cc) and eluted with water. The N-methyl thienamycin derivative elutes in 2–3 column volumes and is lyophilized to a white solid (8 mg)

UV (pH 7 0.1 N phosphate buffer) λ$_{max}$ 298 nm.

IR (Nujol mull) 1755 cm$^{-1}$ (β-lactam).

NMR (100 MHZ, D$_2$O) δ1.29 (d, J=6Hz, C$\underline{H}_3$—CH), 2.68 (S, NCH$_3$), 3.0–3.3 (m, —CH$_2$CH$_2$N, CH$_2$—CS)

3.42 (q, C$_6$H), 4.1–4.5 (m, C$_5$H, C$_7$H).

EXAMPLE 3

N-Acetyl-N-ethyl thienamycin, sodium salt

A solution of N-ethyl thienamycin (8.4 mg) in 7.5 ml of 0.1 N pH 7 phosphate buffer is adjusted to pH 8.3 with 1 N sodium hydroxide solution. Acetic anhydride (0.1 ml) is added and the solution is stirred at room temperature for 15 minutes while maintaining the pH at 8.3 by means of an automatic carrier. The reaction mixture is chromatographed on 15 ml of XAD-2 resin, eluting with water. The product peaks at 2 column volumes and the combined product fractions (UV 84 ODU at λ$_{max}$ 302 nm) are concentrated and freeze dried to a white powder, wt 3.4 mg. Electrophoresis (50 V/cm, 20 min, pH 7) gives a single bioactive zone at +3.5 cm.

EXAMPLE 4

N-Acetyl-N-Methyl thienamycin, sodium salt

Following the procedure of Example 3 except substituting an equivalent amount of N-methyl thienamycin (Example 2) for the N-ethyl thienamycin of Example 3 there is obtained N-acetyl-N-methyl-thienamycin.

EXAMPLE 5

N-Methylthienamycin Benzyl Ester

A solution of N-methylthienamycin (50 mg) in 1 ml of water and 1 ml of dioxane is cooled, to 0° and adjusted to pH 5 with 1 N sulfuric acid. Phenyldiazomethane, (37 mg) in 0.5 ml of dioxane is added during 5 minutes while the pH is maintained at 5 to 5.5 by means of an automatic titrator. The mixture is diluted with water (5 ml) and extracted with ether. The aqueous phase is overlayered with ethylacetate, cooled and adjusted to pH 2.5. The ethylacetate is separated by centrifugation and the aqueous phase is adjusted to 0.48 with sodium bicarbonate and extracted twice with ethylacetate. The extracts are combined and evaporated and the product is isolated by preparative thin layer chromatography on silica gel using 5:1 chloroform-methanol solvent.

EXAMPLE 6

N-Methyl-N-acetyl thienamycin pivaloyloxymethyl ester

A solution of N-methyl-N-acetylthienamycin sodium salt (30 mg) and pivaloyloxymethyl bromide (25 mg) in 0.2 ml of hexamethylphosphoramide is stirred at 23° C. for one hour. Ethylacetate (5 ml) is added and the mixture is extracted successively with aqueous sodium bicarbonate solution, water and saturated sodium chloride solution. The organic phase is dried and evaporaed to a small volume and chromatographed on an 8"×8", 1000μ silica plate using 5:1 chloroform-methanol solution. The band containing N-methyl-N-acetylthienamycin pivaloyloxymethyl ester is scraped off and eluted with ethylacetate.

EXAMPLE 7

N-Ethyl-N-acetylthienamycin 3-methyl-2-butenyl ester hydrochloride

To a solution of N-Ethyl-N-acetylthienamycin (30 mg) in 0.5 ml of 3-methyl-2-butenyl alcohol is added 21 mg of dicyclohexyl carbodiimide. The solution is stirred at 23° C. for one hour then filtered from dicyclohexyl urea. The filtrate is evaporated and the residue chromatographed on an 8"×8" 500μ silica gel plate developed with 1:1 ethylacetate-chloroform.

Following the above procedure but substituting methylthioethanol for 3-methyl-2-butenol there is obtained N-Ethyl-N-acetylthienamycin methylthioethyl ester.

EXAMPLE 8

O, N-Diacetyl-N-ethylthienamycin

N-Ethyl thienamycin (100 mg) is added to a mixture of 0.3 ml of acetic anhydride in 1 ml of pyridine. The mixture is allowed to react at 23° C. for three hours then pumped to dryness under vacuum. The solid residue is dissolved in water and chromatographed on 100 ml of XAD-2 resin. After eluting with water the product is eluted with 10% THF. The fractions containing O,N-diacetyl N-Ethyl thienamycin are combined, evaporated and freeze-dried.

EXAMPLE 9

N-Ethyl-N-acetyl-O-sulfo Thienamycin benzyl Ester

To a solution of N-ethyl-N-acetyl thienamycin benzyl ester (39 mg) in 0.3 ml of pyridine is added sulfur trioxide-pyridine (17 mg). The mixture is stirred at 25° C. for three hours and the excess pyridine is evaporated under reduced pressure. The residue is taken up in 5 ml of water containing 10 mg of sodium bicarbonate and extracted once with ethylacetate. The aqueous solution is concentrated to 2 ml. and chromatographed on 50 g of XAD-2 resin. The fractions containing N-Ethyl-N-acetyl O-sulfo-thienamycin benzyl ester are combined, concentrated and freeze dried.

EXAMPLE 10

N,Ethyl-N-Acetyl-O-sulfo thienamycin sodium salt

A solution of N-Ethyl-N-acetyl-o-sulfo thienamycin benzyl ester (24 mg) in 1 ml of water containing 5 mg of sodium bicarbonate is hydrogenated in the presence of 20 mg of palladium oxide at 23° C. 1 atm pressure for 2 hours. The catalyst is removed by filtration and the filtrate is chromatographed on 20 g of XAD-2 resin. The fractions containing N-ethyl-N-acetyl-O-sulfo-thienamycin sodium salt are combined, concentrated and freeze-dried.

EXAMPLE 11

Th⎯OTMS
  ⎯NHTMS or Th(TMS)₃
  ⎯COOTMS

TMS = trimethylsilyl

Preparation of Silylated-Thienamycin

Thienamycin (80.0 mg.) is suspended in 40 ml. tetrahydrofuran (THF) and under a $N_2$ atmosphere and is concentrated to 10 ml., hexamethyldisilazane (1.0 ml.) and trimethylchlorosilane (300 μl) is added. The mixture is reacted for 20 mins. at 25° C. with vigorous stirring. The suspension is then centrifuged to remove ammonium chloride. The supernatant is evaporated to an oil under a nitrogen stream for furture reaction.

EXAMPLE 12

Preparation of O,N-Dimethyl-N-(p-Nitrobenzyloxycarbonyl)Thienamycin-p-Nitrobenzyl Ester

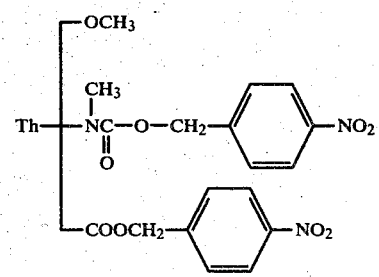

Step A

N-Methyl-N-(p-Nitrobenzyloxycarbonyl) thienamycin Lithium Salt

To N-methyl thienamycin (220 mg. in 60 ml. water at 0° C.) is added successively, 679 mg. $NaHCO_3$, 60 ml dioxane and then with stirring 1.1 equivalents p-nitrobenzylchloroformate over a period of 1.5 minutes. The mixture is allowed to react 10 minutes, and is then extracted three times with cold ethyl ether. Electrophoresis (0.05 M, pH 7, phosphate buffer, 50 V/cm., 20 minutes) shows no free N-methyl thienamycin present. The aq. extract is adjusted to pH 2.2 with 1 M $H_3PO_4$ solution and extracted three times with EtOAc. The EtOAc extract is dried over $MgSO_4$, filtered and reextracted 0.1 N LiOH, to pH 8.2. The final pH is adjusted to 7.0 with 1 M $H_3PO_4$ and the sample lyophilized.

Step B

N-Methyl-N-(p-Nitrobenzyloxycarbonyl) Thienamycin-(p-nitrobenzyl)ester

A mixture of p-nitrobenzyloxycarbonyl-N-methyl-thienamycin lithium salt (295 mg.) and 0.4 g. of p-nitrobenzyl bromide in 3 ml. of hexamethyl phosphoramide is stirred for 3 hours at 25° C. The solution is diluted with 50 ml. of ethyl acetate and extracted successively with water (3 portions), pH 7 phosphate buffer and saturated sodium chloride solution. The organic phase is dried over magnesium sulfate and evaporated to 5 ml. causing the product to crystallize. The crystals are collected and washed with ethyl acetate.

Step C

O,N-Dimethyl-N-(p-Nitrobenzyloxycarbonyl)-thienamycin-(p-Nitrobenzyl ester

To a solution of 135 mg. of N-methyl-N-p-nitrobenzyloxycarbonyl Thienamycin-(p-nitrobenzyl)ester in 50 ml. of methylene chloride at 0° C. is added with vigorous stirring 0.5 ml of 0.006 M fluoboric acid in ether-methylene chloride (3:1) immediately followed by 10 ml. of a cooled solution of 0.6 M diazomethane in methylene chloride. The diazomethane is decolorized in one minute. The solution is extracted with 10 ml of 0.1 N pH 7 phosphate buffer, dried and evaporated to a small volume. The solution is applied to two 8"×8" 1000μ silica gel plates which are developed with 3:1 ethylacetate-chloroform. The band containing O,N-dimethyl N-p-nitrobenzyloxycarbonyl thienamycin p-nitrobenzylester is eluted with ethylacetate and the product is recovered by evaporated of the eluate.

EXAMPLE 13

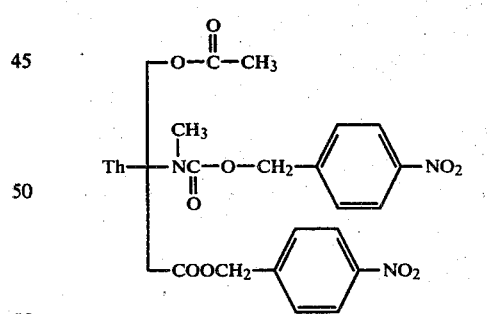

Preparation of O-Acetyl-N-Methyl-N-(p-nitrobenzyloxycarbonyl)-thienamycin-(p-nitrobenzyl)ester To a solution of 50 mg of N-methyl-N-(p-nitrobenzyloxycarbonyl thienamycin) p-nitrobenzylester in 0.5 ml. of pyridine is added 0.16 ml. of acetic anhydride. The mixture is allowed to react at 25° C., for three hours, then pumped to dryness under vacuum. The solid residue is dissolved in chloroform and chromatographed on an 8"×8 1000μ silica gel plate in 3:1 ethylacetate-chloroform yielding o-acetyl-N-methyl-N-p- nitrobenzyloxycarbonyl thienamycin p-nitrobenzyl ester.

EXAMPLE 14

Preparation of O-Acetyl-N-Methyl-N-Azidoacetyl-thienamycin-Benzyl ester

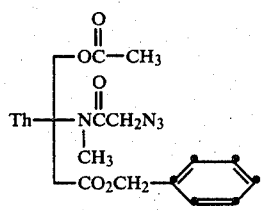

Step A

Preparation of N-Methyl-N-Azidoacetyl-Thienamycin-Sodium (I) and Lithium (II) Salts

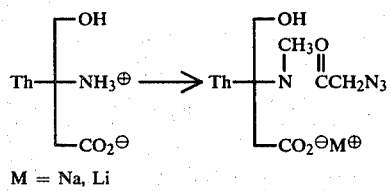

M = Na, Li (I) N-Methyl-thienamycin (48 mg) is dissolved in 10 ml. cold water and is kept at 0°. To the solution is added sodium bicarbonate (147 mg., 17.6 mmol) and dioxane (10 ml.). Azidoacetyl chloride (60 mg., 0.50 mmol) is added to the solution during a period of 2 min. The reaction mixture is stirred for 15 min. then is neutralized to pH 7.0 with 30% phosphoric acid and is transferred into a separatory funnel. The solution is extracted with 2×50 ml of ether.

The aqueous layer is concentrated to 5 ml. and then is charged to a Dowex AG-50×8 (sodium form) ion exchange column monitored by UV. The desired fractions are combined and lyophilized.

N-Methyl-thienamycin (76.2 mg) is dissolved in 10 ml. of cold water and is kept at 0° C. To the solution is added 0.6 ml. of 1.0 N lithium hydroxide solution and 10 ml. dioxane. After stirring for 1 min., azidoacetyl chloride (33.6 mg., 0.28 mmol.) is added during a period of 2 min. The reaction mixture is stirred for additional 1 min. then is neutralized to pH 7.0 with 30% phosphoric acid. After extraction with ether, the aqueous solution is concentrated to 5 ml. and is charged to the Dowex AG-50×8 (lithium form) ion exchange column. The desired fractions are combined and lyophilized.

Step B

Preparation of N-Methyl-N-Azidoacetyl-Thienamycin-Benzyl Ester

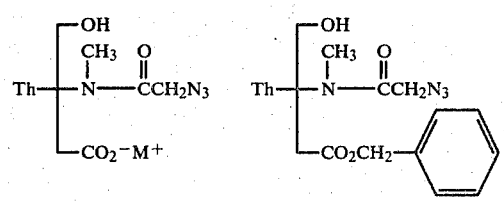

N-Methyl-N-azidoacetyl-thienamycin lithium salt (3.0 mg) is stirred with hexamethylphosphoramide (HMPA) (1.0 ml) and benzyl bromide (30 mg, 0.21 mmol) for 30 min. The reaction mixture is then diluted with ethyl acetate (5 ml) and washed thoroughly with water. The organic layer is separated and dried over sodium sulfate. The product is isolated by silica gel TLC.

STEP C

Preparation of O-Acetyl-N-Methyl-N-Azidoacetyl-Thienamycin Benzyl Ester

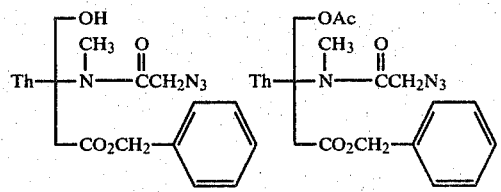

N-Methyl-N-Azidoacetyl-thienamycin benzyl ester (30 mg) is dissolved in 0.5 ml of pyridine. To the solution is added acetic anhydride (0.2 ml). The mixture is kept at room temperature for 40 min. The solution is diluted with 1 ml ethyl acetate and washed with ice-water. The organic layer is separated and dried over sodium sulfate. The desired product is isolated by silica gel TLC.

EXAMPLE 15

Preparation of O-Acetyl-N-Methyl-N-Glycyl Thienamycin

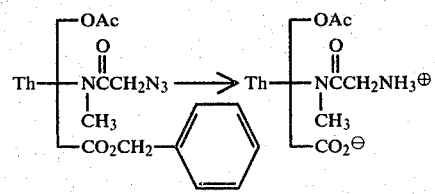

O-Acetyl-N-Methyl-N-Azidoacetyl-Thienamycin-benzyl ester (5.0 mg) is dissolved in 0.3 ml dioxane. The solution is added to a hydrogenation flask containing 20 mg of palladium (from palladium oxide) and 0.5 ml 50% dioxane in water and shaken under 45 psi $H_2$ for 10 mins at 25° C. The catalyst is removed by filtration. After extraction with ether, the solution is lyophilized to give the desired product.

EXAMPLE 16

Preparation of N-Methyl-N-(p-Methoxybenzyloxycarbonyl)thienamycin Sodium Salt

To N-Methyl thienamycin (20 mg) in 5 ml water at 0° C. is added 105 mg NaHCO$_3$, 5 ml. dioxane, and then, dropwise with stirring over 1 min. ten equivalents of p-methoxybenzyl chloroformate. After 15 min. the pH is adjusted to 7.5 with 1 M H$_3$PO$_4$ and the solution extracted 3X with ether. The aqueous portion is then adjusted to pH 2.2 at 0° C. and extracted 3X with ethylacetate (EtOAc). The EtOAc is dried quickly with MgSO$_4$, filtered and extracted with a 7.5 ml of an aqueous solution of NaHCO$_3$ (0.01 M). The extract is lyophilized yielding the product as a light powder.

EXAMPLE 17

Preparation of N-Methyl-N-Bromoacetyl thienamycin Methyl and Benzyl Esters

Step A

N-Methyl-N-Bromoacetyl thienamycin

To a cooled solution of N-Methyl thienamycin (28.8 mg.) and sodium bicarbonate (0.3 g.) in 10 ml. of water and 8 ml. of dioxane is added with stirring a solution of 0.25 g. of bromoacetic anhydride in 2 ml. dioxane over a period of 20 minutes. The pH is maintained at 8.0. The mixture is stirred for an additional 5 minutes then layered with 10 ml. of ether and the pH adjusted to 7 by the additional of 8% phosphoric acid. The ethereal layer is separated and the aqueous layer is extracted twice again with ether. The aqueous layer is evaporated under reduced pressure to 0.5 ml., diluted to 2 ml. with water and put on 50 ml. of XAD-2 resin.

The column is eluted with water. The first 80 ml. is discarded, then the next 100 ml. is collected. The solvent is changed to 10% THF and an additional 100 ml. collected. The combined eluates are adjusted to pH 7, evaporated to 5 ml. under reduced pressure, then freeze-dried to give the sodium salt of N-Methyl-N-bromoacetyl thienamycin.

Step B

N-Methyl-N-Bromoacetyl thienamycin Methyl and Benzyl Esters

An aqueous solution of the sodium salt is layered with ethyl acetate at 0° C. and adjusted to pH 2. The ethyl acetate phase is separated and the aqueous phase is extracted with ethyl acetate. The combined ethyl acetate solutions are dried over MgSO$_4$ and then treated with a solution of diazomethane. The solvents are evaporated and the residue chromatographed on silica gel plate in 2:1 ethyl acetate-chloroform.

The corresponding benzyl ester is prepared in a similar way from phenyldiazonemethane.

EXAMPLE 18

Preparation of N-Methyl-N-benzyloxycarbonyl thienamycin and N-Methyl-N-Benzyloxycarbonyl Thienamycin Benzylcarbonic Acid Anhydride

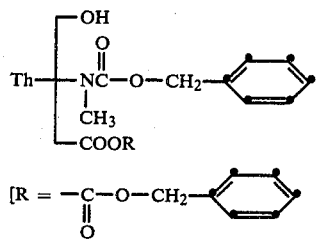

A solution of 16.6 mg of N-methyl thienamycin in 4 ml. of 0.05 M pH 7 phosphate buffer and 2 ml. of dioxane in a 3-necked flask fitted with a stirrer, thermometer, pH electrode and the delivery tip of an automatic titrator is cooled to $-8°$ C. in a methanol-ice bath. The pH is brought to 8.2 by the addition of 0.2 N sodium hydroxide in 50% aqueous dioxane and a solution of 0.015 ml of carbobenzyloxy chloride in 2 ml. of chloroform is added. The mixture is stirred at $-6°$ C., pH 8.2, for ten minutes, then layered with ether and the pH adjusted to 7 by the addition of N hydrochloric acid. The layers are separated by centrifugation and the aqueous phase is extracted twice again with ether. The aqueous phase is layered with ethyl acetate and acidified to pH 2. The ethyl acetate is separated and the aqueous layer is extracted again with ethyl acetate. The combined ethyl acetate layer is washed with saturated sodium chloride solution, dried over magnesium sulfate and filtered. The filtrate is stirred with water and the pH brought to 7 by the addition of dilute sodium bicarbonate solution. The aqueous phase is separated and freeze dried giving the sodium salt of N-Methyl-N-benzyloxycarbonyl thienamycin. The ethereal extracts of the reaction mixture contain the desired product N-methyl-N-benzyloxycarbonyl thienamycin benzyl carbonic acid anhydride.

EXAMPLE 19

N-Allyl-N-Benzenesulfonyl thienamycin

N-Allyl-thienamycin (52 mg) is dissolved in pH 7 0.1 N phosphate buffer (25 ml.) and magnetically stirred in an ice bath. The pH is adjusted to 8.2 with 2.5 N NaOH using an automatic dispensing burette and benzenesulfonyl chloride (227 μl, 226 μmol) in 500 ml. p-dioxane added at once. The pH is maintained at 8.2 (using the automatic burette) for 30 min. and then adjusted to pH 7.0 with dilute aqueous phosphoric acid. The reaction solution is concentrated to 15 ml. and chromatographed on XAD-2 resin (50 cc). The column is eluted with water, then with 10% aqueous tetrahydrofuran which elutes the product. The 10% aqueous tetrahydrofuran eluate is concentrated to ⅓ volume and freeze-dried to give the desired product.

EXAMPLE 20

Preparation of
N-Methyl-N-[N'-Acetimidoyl-β-alanyl]Thienamycin

Step A

N-[β-Azidopropionyl]Thienamycin

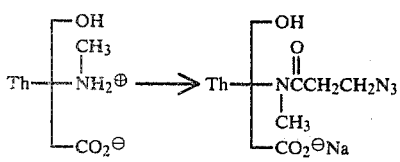

N-Methyl-Thienamycin (184 mg) is dissolved in 30 ml of water and is kept at 0° C. To the solution is added 0.52 g of NaHCO₃, 30 ml of dioxane and 163 mg of β-azidopropionyl chloride. The mixture is stirred for 15 minutes, neutralized with 30% $H_3PO_4$, and extracted with ether. The aqueous layer is separated and concentrated to 5 ml. The crude product is chromatographed on a Dowex 50W×8 (Na form) ion-exchange column (1"×10"). The column is eluted with $H_2O$ to give the desired product.

Step B

N-Methyl-N-(β-Alanyl)Thienamycin

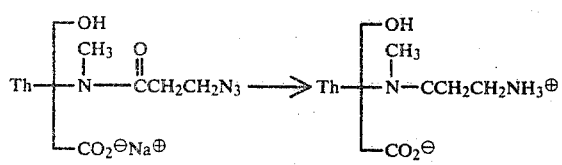

The aqueous solution of N-Methyl-N-(β-azidopropionyl)Thienamycin (40 mg in 20 ml water) is hydrogenated under 1 atm of hydrogen in the presence of 200 mg of palladium at 25° C., for 40 minutes. The resultant solution of (pH 9.0) is neutralized with 30% $H_3PO_4$ and filtered from the catalyst. The mixture is chromatographed on a Dowex 50W×8 (Na form) ion-exchange column (1"×10") and the column is eluted with water to give the desired product.

Step C

N-Methyl-N-[N'-Acetimidoyl-β-alanyl]Thienamycin

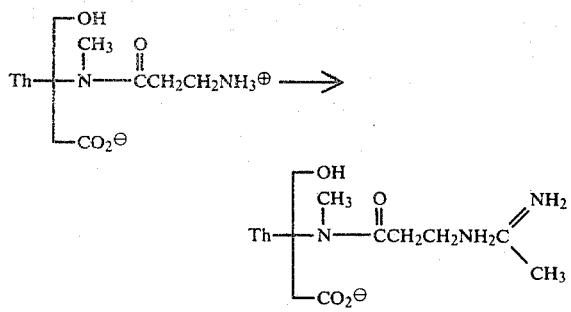

The aqueous solution of N-Methyl-N-(β-alanyl)-thienamycin (125 mg in 15 ml water) is kept at 0° C. and maintained at pH 8.5 by adding 2.5 N NaOH while O-ethylacetimidate hydrochloride (350 mg) is added portionwise to the solution during a period of 10 min. The mixture is stirred for 1 hour then is neutralized with 2.5 N HCl and concentrated to 15 ml. The solution is chromatographed on a Dowex 50W×8 (Na form) column (1"×10") eluted with water. The fractions containing the desired product are combined and lyophilized.

EXAMPLE 21

Preparation of
N-Methyl-N-(Bromo-t-butyloxycarbonyl)Thienamycin Sodium Salt

N-Methyl Thienamycin (190 mg) dissolved in 15 ml 0.1 M pH 7.0 phosphate buffer and 15 ml dioxane is kept at 0° C. The solution is adjusted and maintained between pH 8.5-9.0 with 1 N NaOH while 430 mg of bromo-t-butyl chloroformate is added to the solution during a period of 5 minutes. The mixture is stirred for 30 min., then is neutralized to pH 7.0 with 1 N HCl and extracted with ether. The aqueous layer is separated, concentrated to 10 ml and chromatographed on a Dowex-50×8 (Na form) column (1.5"×10") which is eluted with $H_2O$ to give the desired product.

EXAMPLE 22

Preparation of N-Methyl-N-Acetyl-Thienamycin p-Nitrobenzyl Ester

N-Methyl-N-acetyl thienamycin sodium salt (100 mg) is stirred at 25° C., with p-nitrobenzyl bromide (300 mg) in 2 ml hexamethylphosphoramide for 1 hour. The mixture is diluted with 10 ml ethylacetate and then is washed thoroughly with water. The organic layer is separated, dried over $Na_2SO_4$ and chromatographed on two 250μ silica gel GF TLC plates using ethylacetate as solvent to give the desired product.

EXAMPLE 23

Preparation of O, N-Dimethyl-N-Acetyl Thienamycin

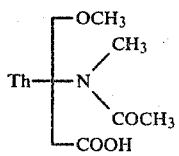

Step A

O, N-Dimethyl-N-Acetyl
Thienamycin-(p-Nitrobenzyl)-Ester

To a solution of 135 mg. of N-Methyl-N-acetyl Thienamycin-p-nitrobenzyl ester in 50 ml. of methylene chloride at 0° C. is added with vigorous stirring 0.5 ml of 0.006 M fluoboric acid in ether-methylene chloride (3:1), immediately followed by 10 ml of a cooled solution of 0.6 M diazomethane in methylene chloride. The diazomethane is decolorized in one minute. The solution is extracted with 10 m. of 0.1 N pH 7 phosphate buffer, dried and evaporated to a small volume. The solution is applied to two 8"×8" 1000μ silica gel plates which are developed with 3:1 ethylacetate-chloroform, yielding O,N-dimethyl-N-acetyl thienamycin-(p-nitrobenzyl)ester.

Step B

O,N-Dimethyl-N-acetyl Thienamycin

A solution of 20 mg. of O, N-Dimethyl N-acetyl thienamycin-p-nitrobenzyl ester in 2 ml of tetrahydrofuran and 1 ml of ethanol is hydrogenated at 50 psig, 23° C. in the presence of 20 mg of platinum oxide for 2½ hours. The catalyst is filtered and 1 ml of 0.1 N pH 7 phosphate buffer is added to the filtrate. The solution is evaporated under reduced pressure to 2 ml. and the mixture is taken up in 5 ml of water and 5 ml of ethylacetate and centrifuged. The ethylacetate layer is removed and the aqueous layer is extracted again with ethylacetate and with ether and then filtered through Celite. The aqueous solution is applied to a column (20 ml) of XAD-2 resin. The column is first eluted with water and then with 10% tetrahydrofuran. The tetrahydrofuran eluate is concentrated and lyophilized giving substantially pure O, N-dimethyl-N-acetyl thienamycin sodium salt.

EXAMPLE 24

Preparation of O-Dibenzylphosphoryl-N-Methyl-N-acetyl Thienamycin-p-nitrobenzyl Ester

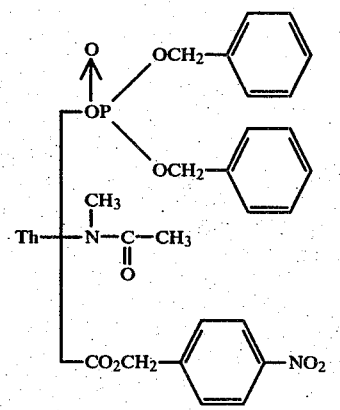

Step A

To a solution of N-Methyl-N-acetyl-thienamycin-(p-nitrobenzyl)ester (50 mg) in 5 ml THF at 3° C. is added 30 mg of dibenzyl phosphorochloridate followed by 14 μl of triethylamine. The mixture is stirred at 25° C. for 2 hours. whereupon the THF is removed in vacuo. The residue is taken up in methylene chloride and washed with water. The methylene chloride solution is dried over magnesium sulfate and evaporated. The residue is chromatographed on silica gel yielding O-dibenzylphosphoryl-N-methyl-N-acetyl thienamycin p-nitrobenzyl ester.

EXAMPLE 25

Preparation of O-(Methylcarbamoyl)-N-Methyl-N-acetyl-Thienamycin-p-nitrobenzyl ester

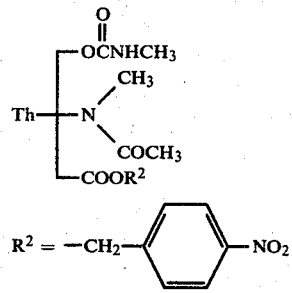

A solution of N-Methyl-N-acetyl thienamycin (p-nitrobenzyl)ester (20 mg) and methylisocyanate (20 mg) in methylene chloride (5 ml) is stirred at 23° C. for 18 hours. The solvent is evaporated and the residue is extracted with hexane. The hexane insoluble residue is chromatographed on silica gel giving substantially pure O-(methylcarbamoyl)-N-Methyl, N-acetyl thienamycin p-nitrobenzyl ester.

EXAMPLE 26

Preparation of O-(Methoxymethyl)-N-Methyl-N-acetyl Thienamycin-p-nitrobenzyl ester

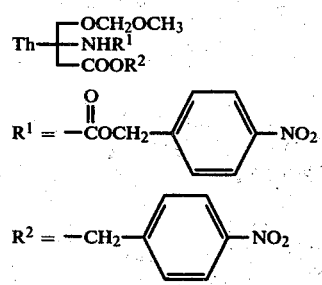

Step A

A solution of 58 mg of N-methyl-N-acetyl thienamycin p-nitrobenzyl ester in 5 ml of 1.0 ml of THF and HMPA is cooled to −78° C. To this solution is added with stirring a 2 N solution of phenyllithium (0.1 ml) immediately followed by the addition of 0.2 ml of methylchloromethyl ether. The mixture is allowed to warm to 25° C. during a period of one hour. Methylene chloride (25 ml) is added and the solution is extracted with 0.1 N, pH 7, phosphate buffer (25 ml) and water 4×25 ml. The methylenechloride solution is evaporated and the residue is triturated with hexane. The hexane insoluble residue is chromatographed on silica gel yielding O-methoxymethyl-N-methyl-N-acetyl thienamycin-(p-nitrobenzyl) ester.

EXAMPLE 27

Preparation of O-Methyl-N-Methyl-N-acetyl thienamycin Benzyl ester

A solution of 5 mg of N-Methyl-N-carbobenzyloxy thienamycin benzyl ester in 0.3 ml of methylene chloride is cooled to 0° C. and 0.1 ml of a 0.006 M solution of fluoboric acid in 5:1 ether-methylene chloride is added, followed immediately by 0.5 ml of 0.1 M diazomethane in methylene chloride. The solution is decolorized in 1 minute. The mixture is stirred with ether and pH 7 phosphate buffer and the ethereal phase is evaporated. The residue is chromatographed on 2×8" 250μ silica plates in 35% ethyl acetate-chloroform yielding the desired product.

EXAMPLE 28

Preparation of N-Thioformyl Thienamycin

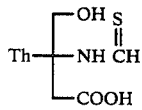

Silylated thienamycin [Th(TMS₃), from 100 mg thienamycin, Example 11] is dissolved in dichloromethane (9 ml) in a stoppered flask under positive nitrogen pressure. To the magnetically stirred solution is added a solution of triethylamine (60 μl) in dichloromethane (1 ml). This is followed by the addition of ethyl thioformate (100 μl). After 1 hour the reaction solution is rapidly added to a stirred solution of pH 4 0.1 N phosphate buffer (20 ml). The mixture is stirred 5 minutes and the pH of the mixture adjusted to 7.0 with 1 N NaOH. The aqueous phase is separated, washed with ethyl acetate (2×20 ml) and cooled in an ice bath. The solution is layered with ethylacetate (15 ml) and the pH of the stirred mixture is adjusted to 3.5 with 1 N phosphoric acid. The organic phase is separated and the buffered aqueous solution washed with ethyl acetate (2×15 ml). The combined ethyl acetate washings are concentrated to half volume and layered with water (10 ml). Solid sodium bicarbonate is added until the pH of the mixture is 7.0. The aqueous phase is separated and lyophilized to give the sodium salt of N-thioformyl thienamycin.

EXAMPLE 29

Following the procedures set forth above, the following compounds of the present invention (Table I) are obtained when the indicated N-alkylated starting material is N-acylated with the reagent calculated to provide the species represented in the Table.

TABLE I $$\text{structure with } OR^3, SCH_2CH_2NR^1R^2, COXR^4$$

| Compound | $R^1$ | $R^2$ | $R^3$ | $R^4$ | X | |
|---|---|---|---|---|---|---|
| 1. | | $CH_3$ | $-CHO$ | H | Na | 0 |
| 2. | | $CH_3$ | $-C(=O)-OCH_3$ | H | Na | 0 |
| 3. | | $CH_3$ | $-C(=O)-CH_2NH_2$ | H | H | 0 |
| 4. | | $CH_3$ | $-C(=O)-CH(H)-N-C(CH_3)=NH$ | H | H | 0 |
| 5. | | $CH_3$ | $-C(=O)-N(H)-CH_3$ | H | Na | 0 |
| 6. | | $CH_3$ | $-C(=O)-CH_2Cl$ | H | Na | 0 |
| 7. | | $CH_3$ | $-C(=O)-CH_2CH_2NH_2$ | H | H | 0 |
| 8. | | $CH_3$ | $-C(=O)-CH_2CH=CH_2$ | H | Na | 0 |
| 9. | | $CH_3$ | $-C(=O)-CH_2-N=C(H)-NH_2$ | H | H | 0 |
| 10. | | $CH_3$ | $-C(=O)-CH_2N(H)-C(NH)(NH_2)$ | H | H | 0 |
| 11. | | $CH_3$ | $-C(=O)-CH_2N(CH_3)_3$ | H | — | 0 |
| 12. | | $CH_3$ | $-C(=O)-O-CH_2\phi$ | H | Na | 0 |
| 13. | | $CH_3$ | $-C(=O)-CF_3$ | H | Na | 0 |
| 14. | | $CH_3$ | $-C(=O)-C\equiv CH$ | H | Na | 0 |

TABLE I-continued $$\text{structure with } OR^3, \; SCH_2CH_2NR^1R^2, \; COXR^4, \; \beta\text{-lactam N, C=O}$$

| Compound | R¹ | R² | R³ | R⁴ | X | |
|---|---|---|---|---|---|---|
| 15. | | CH₃ | —C(=O)—S—CH₃ | H | Na | 0 |
| 16. | | CH₃ | —CHO | —CHO | Na | 0 |
| 17. | | CH₃ | —C(=O)—CH₃ | —C(=O)—CH₃ | —CH₂O—C(=O)—C(CH₃)₃ | 0 |
| 18. | | CH₃ | —C(=O)—CH₃ | —C(=O)—CH₃ | K | 0 |
| 19. | | CH₃ | —C(=O)—CH₃ | —SO₃Na | Na | 0 |
| 20. | | CH₃ | —C(=O)—CH₃ | PO₃HNa | Na | 0 |
| 21. | | CH₃ | —C(=O)—CH₃ | —C(=O)—NHCH₃ | K | 0 |
| 22. | | CH₃ | —C(=O)—CH₃ | —CH₂OCH₃ | Na | 0 |
| 23. | | CH₃ | —C(=O)—CH₃ | H | —CH₂C(H)=C(CH₃)—CH₃ | O |
| 24. | | CH₃ | —CHO | H | —CH₂O—C(=O)—(CH₃)₃ | 0 |
| 25. | | CH₃ | —C(=O)—CH₂—S—C(=NH)NH₂ | H | H | O |
| 26. | | CH₃ | —CHO | SO₂NH₂ | Na | O |
| 27. | | CH₃ | —C(=O)—CH₃ | CH₃ | Na | 0 |
| 28. | | CH₃ | —C(=O)—CH₃ | CH₃ | —CH₂OC(=O)—C(CH₃)₃ | 0 |
| 29. | | C₂H₅ | —C(=O)—CH₂NH₂ | H | H | 0 |
| 30. | | C₂H₅ | —C(=O)—CH(H)—N=C(CH₃)—NH | H | H | 0 |
| 31. | | C₂H₅ | —C(=O)—O—CH₃ | H | Na | 0 |
| 32. | | C₂H₅ | —C(=O)—NH—CH₃ | H | Na | 0 |
| 33. | | CH₃ | —C(=S)—N(H)—CH₃ | H | Na | 0 |
| 34. | | CH₃ | —C(=S)—H | H | Na | 0 |
| 35. | | CH₃ | —C(=S)—H | H | —CH₂CH₂—S—CH₃ | 0 |
| 36. | | CH₃ | —C(=O)—N(H)—C(=NH)—NH₂ | H | H | 0 |
| 37. | | CH₃ | —CHO | H | —CH₂φ—NO₂ | O |

TABLE I-continued

[Structure shown with OR³, SCH₂CH₂NR¹R², COXR⁴ substituents on bicyclic β-lactam core]

| Compound | R¹ | R² | R³ | R⁴ | X |
|---|---|---|---|---|---|
| 38. | | CH₃ | −P(=O)(ONa)(OCH₃) | H | Na | 0 |
| 39. | −CH₂−CH=CH₂ | | −C(=O)−CH₃ | H | Na | O |
| 40. | −CH₂φ | | −CHO | H | Na | 0 |

EXAMPLE 30
Preparation of Pharmaceutical Compositions

One such unit dosage form consists in mixing N-methyl-N-acetyl-thienamycin with 20 mg of lactose and 5 mg of of magnesium stearate and placing the 145 mg mixture into a No. 3 gelatin capsule. Similarly, by employing more of the active ingredient and less lactose, other dosage forms can be put up in No. 3 gelatin capsules and should it be necessary to mix more than 145 mg of ingredients together, larger capsules such as compressed tablets and pills can also be prepared. The following examples are illustrative of the preparation of pharmaceutical formulations:

| TABLET | PER TABLET |
|---|---|
| N-methyl-N-acetyl thienamycin | 125 mg. |
| Cornstarch, U.S.P. | 6 mg. |
| Dicalcium Phosphate | 192 mg. |
| Lactose, U.S.P. | 190 mg. |
| Magnesium Stearate | Balance/800 mg |

The active ingredient is blended with the dicalcium phosphate, lactose and about half of the cornstarch. The mixture is then granulated with 15% cornstarch paste (6 mg) and rough-screened. It is dried at 45° C. and screened again through No. 16 screens. The balance of the cornstarch and magnesium stearate is added and the mixture is compressed into tablets, approximately 0.5 inch in diameter each weighing 800 mg.

| PARENTERAL SOLUTION | PER TABLET |
|---|---|
| Ampoule: | |
| N-methyl-N-Acetyl Thienamycin | 500 mg. |
| Diluent: Sterile Water for Injection | 2 cc. |
| OPTHALMIC SOLUTION | |
| N-methyl-N-Acetyl-Thienamycin | 100 mg. |
| Hydroxypropylmethyl Cellulose | 5 mg. |
| Sterile Water to | 1 ml. |
| OTIC SOLUTION | |
| N-methyl-N-Acetyl-Thienamycin | 100 mg. |
| Benzalkonium Chloride | 0.1 mg. |
| Sterile Water to | 1 ml. |
| TOPICAL OINTMENT | |
| N-methyl-N-Acetyl-Thienamycin | 100 mg. |
| Polyethylene Glycol 4000 U.S.P. | 400 mg. |

| PARENTERAL SOLUTION | PER TABLET |
|---|---|
| Polyethylene Glycol 400 U.S.P. | 1.0 gram |

The active ingredient in the above formulations may be administered alone or in combination with other biologically active ingredients as, for example, with other antibacterial agents such as lincomycin, a penicillin, streptomycin, novobiocin, gentamicin, neomycin, colistin and kanamycin, or with other therapeutic agents such as probenecid.

What is claimed is:

1. A compound having the structural formula:

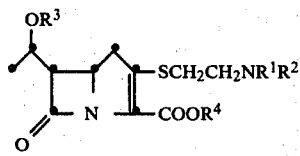

and the pharmaceutically acceptable salts thereof wherein:

R¹ is selected from the group consisting of loweralkyl; loweralkenyl and benzyl;

R⁴ is selected from the group consisting of hydrogen, methyl, t-butyl, phenacyl, p-bromophenacyl; pivaloyloxymethyl, 2,2,2-trichloroethyl, allyl, 3-methyl-2-butenyl, 2-methyl-2-propenyl, benzyl, benzylhydryl, p-t-butylbenzyl, phthalidyl, phenyl, 5-indanyl, acetylthiomethyl, acetoxymethyl, propionyloxymethyl, methallyl, 3-butenyl, 4-pentenyl, 2-butenyl, acetoxyacetylmethyl, pivaloylacetylmethyl, diethylaminoethyl, dimethylaminoethyl, methoxymethyl, p-acetoxybenzyl, p-pivaloylbenzyl, p-isopropoxybenzyl, 5-indanylmethyl, benzyloxymethyl, methylthioethyl, dimethylaminoacetoxymethyl, crotonolacton-3-yl, acetamidomethyl, acetylthioethyl, pivaloylthiomethyl and methylthiomethyl;

R³ is selected from the group consisting of hydrogen, loweralkyl and loweralkanoyl; and R² is selected from the group consisting of formyl, loweralkoxycarbonyl, benzyloxycarbonyl, loweralkenylcarbonyl, loweralkynylcarbonyl and loweralkanoyl which may be substituted by halo, amino, mono- or diloweralkylamino, guanidino or carbamoyl.

2. A compound according to claim 1 wherein $R^1$ is loweralkyl.

3. A compound according to claim 1 wherein $R^3$ is hydrogen and $R^4$ is hydrogen.

4. A compound according to claim 1 wherein $R^1$ is methyl or ethyl.

5. A compound according to claim 1 wherein $R^1$ is methyl, $R^2$ is acetyl, $R^3$ is hydrogen and $R^4$ is hydrogen.

6. An antibiotic pharmaceutical composition consisting essentially of, in unitary dosage form, a therapeutically effective amount of a compound according to claim 1 and a pharmaceutical carrier therefor.

* * * * *